US006153729A

United States Patent [19]
Stein et al.

[11] Patent Number: 6,153,729
[45] Date of Patent: Nov. 28, 2000

[54] ISOLATED NUCLEAR MATRIX TARGETING PEPTIDE

[75] Inventors: Gary S. Stein, Shrewsbury; Andre J. van Wijnen, Auburn; Janet L. Stein, Shrewsbury; Jane B. Lian, Milton, all of Mass.; Jeanne Lawrence, Mapleville, R.I.; Cong-Mei Zeng, Topsfield; Lindsay Shopland, Hopkinton, both of Mass.; Scott Hiebert, Brentwood, N.J.; Shari Meyers, Shreveport, La.; Sheldon Penman, Brookline, Mass.

[73] Assignees: St. Jude's Children's Research Hospital, Memphis, Tenn.; University of Massachusetts, Worcester, Mass.

[21] Appl. No.: 09/100,193

[22] Filed: Jun. 19, 1998

Related U.S. Application Data

[60] Provisional application No. 60/050,104, Jun. 20, 1997.

[51] Int. Cl.[7] .............................. C07K 14/47; C07H 21/00
[52] U.S. Cl. .......................... 530/300; 530/324; 530/350; 536/23.1
[58] Field of Search .................................. 530/300, 324, 530/350; 536/23.1

[56] References Cited

U.S. PATENT DOCUMENTS 5,580,727  12/1996  Ohki et al. .

FOREIGN PATENT DOCUMENTS

| 930147854 | 6/1993 | Japan . |
| WO 95/31557 | 11/1995 | WIPO . |
| WO 95/34295 | 12/1995 | WIPO . |

OTHER PUBLICATIONS

Berendsen, Science, vol. 282: pp. 642–643, Oct. 1998.
van Wijnen, A.J. et al. "Developmental Control of Trans–activation and Subnuclear Location in Osteoblasts: Identification of a Nuclear Matrix Targeting Domain in the AML–1/CBF–α/RUNT Transcription Factor" Journal of Bone and Mineral Research 11(Supp. 1):S393 (1996).
Zeng, C. et al., "Identification of a Nuclear Matrix Targeting Signal in the Leukemia and Bone–related AML/CBF–α Transcription Factors" Proc. Natl. Acad. Sci. USA 94:6746–6751 (1997).
Bae, S.C. et al., "Isolation of PEB2αB cDNA Representing the Mouse Homolog of Human Acute Myeloid Leukemia Gene AML1," Oncogene, vol. 8, No. 3, 809–14 (1993).
Banerjee, C. et al., "An AML–1 Consensus Sequence Binds an Osteoblast–Specific Complex and Transcriptionally Activates the Osteocalcin Gene," PNAS, vol. 93, 4968–73 (1996).
Berger, J. et al., "Secreted Placental Alkaline Phosphatase: a Powerful New Quantitative Indicator of gene Expression in Eukaryotic Cells," Gene, vol. 66, 1–10 (1988).

Bidwell, J. et al., "Osteocalcin Gene Promoter–binding Factors are Tissue–specific Nuclear Matrix Components," PNAS, vol. 90, 3162–6 (1993).
Blencowe, B.J. et al., "Association of Nuclear Matrix Antigens with Exon–Containing Splicing Complexes," J. Cell Biol., vol. 127, 593–607 (1994).
Brown, C.J. et al., "The Human XIST Gene: Analysis of a 17 kb Inactive X–Specific RNA That Contains Conserved Repeats and is Highly Localized within the Nucleus," Cell, vol. 71, 527–42 (1992).
Buhrmester, H. et al., "Nuclear Matrix Protein ARBP Recognizes a Novel DNA Sequence Motif with High Affinity," Biochemistry, vol. 34, 4108–17 (1995).
Carter, K.C. et al., "A Three–Dimensional View of Precursor Messenger RNA Metabolism Within the Mammalian Nucleus," Science, vol. 259, 1330–5 (1993).
Carvalho, T. et al., "Targeting of Adenovirus E1A and E4–ORF3 Proteins to Nuclear Matrix–associated PML Bodies," J. Cell. Biol., vol. 131, 45–56 (1995).
Clemson, C.M. et al., "XIST RNA Paints the Inactive X Chromosome at Interphase: Evidence for a Novel RNA Involved in Nuclear/Chromosome Structure," J. Cell Biol., vol. 132, 259–75 (1996).
Dickinson, L.A. et al., "A Tissue–Specific MAR/SAR DNA–Binding Protein with Unusual Binding Site Recognition," Cell, vol. 70, 631–45 (1992).
Downing, J.R. et al., "An AML1/ETO Fusion Transcript is Consistently Detected by RNA–Based Polymerase Chain Reaction in Acute Myelogenous Leukemia Containing the (8;21)(q22;q22) Translocation," Blood, vol. 81, No. 11, 2860–5 (1993).
Dyck, J.A. et al., "A Novel Macromolecular Structure is a Target of the Promyelocyte–Retinoic Acid Receptor Oncoprotein," Cell, vol. 76, 333–43 (1994).
Erickson, P. et al., "Identification of Breakpoints in t(8;21) Acute Myelogenous Leukemia and Isolation of a Fusion Transcript, AML1/ETO, with Similarity to Drosophila Segmentation Gene, runt," Blood, vol. 80, No. 7, 1825–31 (1992).
Fakan, S., "Perichromatin Fibrils are in situ Forms of Nascent Transcripts," Trends Cell Biol., vol. 4, 86–90 (1994).
Fey, E.G. et al., "Epithelial Cytoskeletal Framework and Nuclear Matrix–Intermediate Filament Scaffold: Three–dimensional Organization and Protein Composition," J. Cell. Biol., vol. 98, 1973–84 (1984).
Frank, R. et al., "The AML1/ETO Fusion Protein Blocks Transactivation of the GM–CSF Promoter by AML1B," Oncogene, vol. 11, 2667–74 (1995).

(List continued on next page.)

Primary Examiner—Terry McKelvey
Attorney, Agent, or Firm—Lahive & Cockfield, LLP; Jane E. Remillard, Esq.; Amy E. Mandragouras, Esq.

[57] ABSTRACT

Nuclear matrix targeting peptides (NMTPs) capable of delivering a variety of therapeutic and diagnostic agents, such as transcription regulatory factors, to the nuclear matrix of a cell are disclosed.

5 Claims, 6 Drawing Sheets

OTHER PUBLICATIONS

Giese, K. et al., "Assembly and Function of a TCRα Enhancer Complex is Dependent on LEF–1–induced DNA Bending and Multiple Protein–Protein Interactions," *Genes Dev.*, vol. 9, 995–1008 (1995).

Golub, T.R. et al., "Fusion of the TEL Gene on 12p13 to the AML1 Gene on 21q22 in Acute Lymphoblastic Leukemia," *PNAS*, vol. 92, 4917–21 (1995).

Gottschalk, L.R. and Leiden, J.M., "Identification and Functional Characterization of the Human T–Cell Receptor β Gene Transcriptional Enhancer: Common Nuclear Proteins Interact with the Transcriptional Regulatory Elements of the T–Cell Receptor α and β Genes," *Mol. Cell. Biol.*, vol. 10, No. 10, 5486–95 (1990).

Guo, B. et al., "The Nuclear Matrix Protein NMP–1 is the Transcription Factor YY1," *PNAS*, vol. 92, 10526–30 (1995).

Hernandez–Munain, C. and Krangel, M.S., "Regulation of the T–Cell Receptor δ Enhancer by Functional Cooperation Between c–Myb and Core–Binding Factors," *Mol. Cell. Biol.*, vol. 14, No. 1, 473–83 (1994).

Hiebert, S.W. et al., "The t(12;21) Translocation Converts AML–1B from an Activator to a Repressor of Transcription," *Mol. Cell. Biol.*, vol. 16, No. 4, 1349–55 (1996).

Ho, I.–C. et al., "A T–Cell–Specific Transcriptional Enhancer Element 3' of Cα in the Human T–Cell Receptor α Locus," *PNAS*, vol. 86, 6714–8 (1989).

Kurokawa, M. et al., "A Conserved Cysteine Residue in the runt Homology Domain of AML1 is Required for the DNA Binding Ability and the Transforming Activity on Fibroblasts," *J. Biol. Chem.*, vol. 271, No. 28, 16870–6 (1996).

Lenny, N. et al., "Functional Domains of the t(8;21) Fusion Protein, AML–1/ETO," *Oncogene*, vol. 11, 1761–9 (1995).

Lenny, N. et al., "The AML Family of Transcription Factors Associates with the Nuclear Matrix and this Association is Necessary for Transcriptional Activation," *Blood*, vol. 86, No. 10, 2375 (1995).

Leonhardt, H. et al., "A Targeting Sequence Directs DNA Methyltransferase to Sites of DNA Replication in Mammalian Nuclei," *Cell*, vol. 71, 865–73 (1992).

Levanon, D. et al., "AML1, AML2, and AML3, the Human Members of the runt domain Gene–Family: cDNA Structure, Expression, and Chromosomal Localization," *Genomics*, vol. 23, 425–32 (1994).

Lu, J. et al., "Subcellular Localization of the α and β Subunits of the Acute Myeloid Leukemia–Linked Transcription Factor PEBP2/CBF," *Molecular and Cellular Biology*, vol. 15, No. 1651–61 (1995).

Ludérus, M.E.E. et al., "Binding of Matrix Attachment Regions to Lamin B1," *Cell*, vol. 70, 949–59 (1992).

Ludérus, M.E.E. et al., "Binding of Matrix Attachment Regions to Lamin Polymers Involves Single–Stranded Regions and the Minor Groove," *Mol. Cell. Biol.*, vol. 14, No. 9, 6297–6305 (1994).

Mancini, M.A. et al., "The Retinoblastoma Gene Product is a Cell Cycle–Dependent, Nuclear Matrix–Associated Protein," *PNAS*, vol. 91, 418–22 (1994).

Matera, A.G. and Ward, D.C., "Nucleoplasmic Organization of Small Nuclear Ribonucleoproteins in Cultured Human Cells," *J. Cell Biol.*, vol. 121, No. 4, 715–27 (1993).

Merriman, H. et al., "The Tissue–Specific Nuclear Matrix Protein, NMP–2, is a Member of the AML/CBF/PEBP2/ Runt Domain Transcription Factor Family: Interactions with the Osteocalcin Gene Promoter," *Biochemistry*, vol. 34, 13125–32 (1995).

Meyers, S. et al., "AML–2 is a Potential Target for Transcriptional Regulation by the t(8;21) and t(12;21) Fusion Proteins in Acute Leukemia," *Oncogene,*, vol. 13, 303–12 (1996).

Meyers, S. et al., "Identification of AML–1 and the (8;21) Translocation Protein (AML–1/ETO) as Sequence–Specific DNA–Binding Proteins: the runt Homology Domain is Required for DNA Binding and Protein–Protein Interactions," *Molecular and Cellular Biology*, vol. 13, No. 10, 6336–45 (1993).

Meyers, S. et al., "The t(8;21) Fusion Protein Interferes with AML–1B–Dependent Transcriptional Activation," *Molecular and Cellular Biology*, vol. 15, No. 4, 1974–82 (1995).

Mitani, K. et al., "Generation of the AML1–EVI–1 Fusion Gene in the t(3;21)(q26;q22) Causes Blastic Crisis in Chronic Myelocytic Leukemia," *EMBOJ*, vol. 13, No. 3, 504–10 (1994).

Miyoshi, H. et al., "Alternative Splicing and Genomic Structure of the AML1 Gene Involved in Acute Myeloid Leukemia," *Nucl. Acids. Res.*, vol. 23, No. 14, 2762–9 (1995).

Miyoshi, H. et al., "t(8;21) Breakpoints of Chromosome 21 in Acute Myeloid Leukemia are Clustered Within a Limited Region of a Single Gene, AML1," *PNAS*, vol. 88, 10431–4 (1991).

Miyoshi, H. et al., "The t(8;21) Translocation in Acute Myeloid Leukemia Results in Production of and AML1–MTG8 Fusion Transcript," *EMBOJ*, vol. 12, No. 7, 2715–21 (1993).

Nickerson, J.A. et al., The Architectural Organization of Nuclear Metabolism, eds. Berezney, R. and Jeon, K.W., 67–123 (1995).

Nimer, S. et al., "Transcriptional Regulation of Interleukin–3 Expression in Megakaryocytes," *Blood*, vol. 88, No. 1, 66–74 (1996).

Nisson, P.E. et al., "Transcriptionally Active Chimeric Gene Derived from the Fusion of the AML1 Gene and a Novel Gene on Chromosome 8 in t(8;21)Leukemic Cells," *Cancer Genet. Cylogenet.*, vol. 63, 81–8 (1992).

Nuchprayoon, I. et al., "PEBP2/CBF, the Murine Homolog of the Human Myeloid AML1 and PEBP2β/CBFβ Proto–oncoproteins, Regulates the Murine Myeloperoxidase and Neutrophil Elastase Genes in Immature Myeloid Cells," *Mol. Cell. Biol.*, vol. 14, No. 8, 5555–68 (1994).

Nucifora, G. et al., "Involvement of the AML1 Gene in the t(3;21) in Therapy–Related Leukemia and in Chronic Myeloid Leukemia in Blast Crisis," *Blood*, vol. 81, No. 10, 2728–34 (1993).

Ogawa, E. et al., "Molecular Cloning and Characterization of PEBP2β, the Heterodimeric Partner of a Novel Drosophila runt–Related DNA Binding Protein PEBP2α," *Virology*, vol. 194, 314–31 (1993).

Ogawa, E. et al., "PEBP2/PEA2 Represents a Family of Transcription Factors Homologous to the Products of the Drosophila runt Gene and the Human AML1 Gene," *PNAS*, vol. 90, 6859–63 (1993).

Radu, A. et al., "Identification of a Protein Complex that is Required for Nuclear Protein Import and Mediates Docking of Import Substrate to Distinct Nucleoporins," *PNAS*, vol. 92, 1769–73 (1995).

Romana, S.P. et al., "High Frequency t(12;21) in Childhood B–Lineage Acute Lymphoblastic Leukemia," *Blood*, vol. 86, No. 11, 4263–9 (1995).

Romana, S.P. et al., "The t(12;21) of Acute Lymphoblastic Leukemia Results in a tel–AML1 Gene Fusion," *Blood*, vol. 85, No. 12, 3662–70 (1995).

Rubin, C.M. et al., "t(3;21)(q26;q22): A Recurring Chromosomal Abnormality in Therapy–Related Myelodysplastic Syndrome and Acute Myeloid Leukemia," *Blood*, vol. 76, No. 12, 2594–8 (1990).

Satake, M. et al., "Expression of the Runt Domain–Encoding PEBP2α Genes in T Cells During Thymic Development," *Mol. Cell. Biol.*, vol. 15, No. 3, 1662–70 (1995).

Scheer, U. et al., "Structure, Function and Assembly of the Nucleolus," *Trends Cell Biol.*, vol. 3, 236–41 (1993).

Silver, P.A. et al., "Amino Terminus of the Yeast GAL4 Gene Product is Sufficient for Nuclear Localization," *PNAS*, vol. 81, 5951–5 (1984).

Spector, D.L., "Macromolecular Domains Within the Cell Nucleus," *Annu. Rev. Cell. Biol.*, vol. 9, 265–315 (1993).

Stein, G.S. et al., "Nuclear Architecture Supports Integration of Physiological Regulatory Signals for Transcription of Cell Growth and Tissue–Specific Genes During Osteoblast Differentiation," *J. Cell. Biochem.*, vol. 55, 4–15 (1994).

Stuurman, N. et al., "A Monoclonal Antibody Recognizing Nuclear Matrix–associated Nuclear Bodies," *J. Cell. Sci.*, vol. 101, 773–84 (1992).

Takahashi, A. et al., "Positive and Negative Regulation of Granulocyte–Macrophage Colony–Stimulating Factor Promoter Activity by AML1–Related Transcription Factor, PEBP2," *Blood*, vol. 86, No. 2, 607–16 (1995).

van Wijnen, A.J. et al., "Developmental Control of Trans––Activation and Subnuclear Location in Osteoblasts: Identification of a Nuclear Matrix Targeting Domain in the AML–1/CBF–α/Runt Transcription Factor," *Journal of Bone and Mineral Research*, vol. 11, supp 1, S393, (1996).

van Wijnen, A.J. et al., "Nuclear Matrix Association of Multiple Sequence–Specific DNA Binding Activities Related to SP–1, ATF, CCAAT, C/EBP, OCT–1 and AP–1," *Biochemistry*, vol. 32, 8397–8402 (1993).

von Kries, J.P. et al., "A Matrix/Scaffold Attachment Region Binding Protein: Identification, Purification, and Mode of Binding," *Cell*, vol. 64, 123–35 (1991).

Wang, S. et al., "Cloning and Characterization of Subunits of the T–Cell Receptor and Murine Leukemia Virus Enhancer Core–Binding Factor," *Mol. Cell. Biol.*, vol. 13, No. 6, 3324–39 (1993).

Weis, K. et al., "Retinoic Acid Regulates Aberrant Nuclear Localization of PML–RARα in Acute Promyelocytic Leukemia Cells," *Cell*, vol. 76, 345–56 (1994).

Wotton, D. et al., "Cooperative Binding of Ets–1 and Core Binding Factor to DNA," *Mol. Cell. Biol.*, vol. 14, No. 1, 840–50 (1994).

Xing, Y. et al., "Higher Level Organization of Individual Gene Transcription and RNA Splicing," *Science*, vol. 259, 1326–30 (1993).

Zeng et al., "Intranuclear Targeting of AML/CBFα Regulatory Factors to Nuclear Matrix–associated Transcriptional Domains," *PNAS*, vol. 95, 1585–9 (1988).

Zeng, C. et al., "Targeting of the AML–1/CBF–α Runt Transcription Factor to the Nuclear Matrix," *Molecular Biology of the Cell*, vol. 7, supp., 2778 (1996).

Zhang, D.E. et al., "CCAAT Enhancer–Binding Protein (C/EBP) and AML1 (CBFα2) Synergistically Activate the Macrophage Colony–Stimulating Factor Receptor Promoter," *Mol. Cell. Biol.*, vol. 16, No. 3, 1231–40 (1996).

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 480 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO: 1:

```
Met Ala Ser Asp Ser Ile Phe Glu Ser Phe Pro Ser Tyr Pro Gln Cys
1               5                   10                  15

Phe Met Arg Glu Cys Ile Leu Gly Met Asn Pro Ser Arg Asp Val His
            20                  25                  30

Asp Ala Ser Thr Ser Arg Arg Phe Thr Pro Pro Ser Thr Ala Leu Ser
        35                  40                  45

Pro Gly Lys Met Ser Glu Ala Leu Pro Leu Gly Ala Pro Asp Ala Gly
    50                  55                  60

Ala Ala Leu Ala Gly Lys Leu Arg Ser Gly Asp Arg Ser Met Val Glu
65                  70                  75                  80

Val Leu Ala Asp His Pro Gly Glu Leu Val Arg Thr Asp Ser Pro Asn
                85                  90                  95

Phe Leu Cys Ser Val Leu Pro Thr His Trp Arg Cys Asn Lys Thr Leu
            100                 105                 110

Pro Ile Ala Phe Lys Val Val Ala Leu Gly Asp Val Pro Asp Gly Thr
            115                 120                 125

Leu Val Thr Val Met Ala Gly Asn Asp Glu Asn Tyr Ser Ala Glu Leu
    130                 135                 140

Arg Asn Ala Thr Ala Ala Met Lys Asn Gln Val Ala Arg Phe Asn Asp
145                 150                 155                 160

Leu Arg Phe Val Gly Arg Ser Gly Arg Gly Lys Ser Phe Thr Leu Thr
                165                 170                 175

Ile Thr Val Phe Thr Asn Pro Pro Gln Val Ala Thr Tyr His Arg Ala
            180                 185                 190

Ile Lys Ile Thr Val Asp Gly Pro Arg Glu Pro Arg Arg His Arg Gln
            195                 200                 205

Lys Leu Asp Asp Gln Thr Lys Pro Gly Ser Leu Ser Phe Ser Glu Arg
    210                 215                 220

Leu Ser Glu Leu Glu Gln Leu Arg Arg Thr Ala Met Arg Val Ser Pro
225                 230                 235                 240

His His Pro Ala Pro Thr Pro Asn Pro Arg Ala Ser Leu Asn His Ser
                245                 250                 255

Thr Ala Phe Asn Pro Gln Pro Gln Ser Gln Met Gln Asp Thr Arg Gln
            260                 265                 270

Ile Gln Pro Ser Pro Pro Trp Ser Tyr Asp Gln Ser Tyr Gln Tyr Leu
            275                 280                 285

Gly Ser Ile Ala Ser Pro Ser Val His Pro Ala Thr Pro Ile Ser Pro
    290                 295                 300

Gly Arg Ala Ser Gly Met Thr Thr Leu Ser Ala Glu Leu Ser Ser Arg
305                 310                 315                 320

Leu Ser Thr Ala Pro Asp Leu Thr Ala Phe Ser Asp Pro Arg Gln Phe
                325                 330                 335

Pro Ala Leu Pro Ser Ile Ser Asp Pro Arg Met His Tyr Pro Gly Ala
            340                 345                 350

Phe Thr Tyr Ser Pro Thr Pro Val Thr Ser Gly Ile Gly Ile Gly Met
            355                 360                 365

Ser Ala Met Gly Ser Ala Thr Arg Tyr His Thr Tyr Leu Pro Pro Pro
    370                 375                 380

Tyr Pro Gly Ser Ser Gln Ala Gln Gly Gly Pro Phe Gln Ala Ser Ser
385                 390                 395                 400
```

```
Pro Ser Tyr His Leu Tyr Tyr Gly Ala Ser Ala Gly Ser Tyr Gln Phe
            405                 410                 415

Ser Met Val Gly Gly Glu Arg Ser Pro Pro Arg Ile Leu Pro Pro Cys
            420                 425                 430

Thr Asn Ala Ser Thr Gly Ser Ala Leu Leu Asn Pro Ser Leu Pro Asn
            435                 440                 445

Gln Ser Asp Val Val Glu Ala Glu Gly Ser His Ser Asn Ser Pro Thr
450                 455                 460

Asn Met Pro Ala Ser Ala Arg Leu Glu Glu Ala Val Trp Arg Pro Tyr
465                 470                 475                 480
```

(2) INFORMATION FOR SEQ ID NO: 2:

(i) SEQUENCE CHARACTERISTICS:
      (A) LENGTH: 415 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO: 2:

```
Met Arg Ile Pro Val Asp Pro Ser Thr Ser Arg Arg Phe Thr Pro Pro
1               5                   10                  15

Ser Pro Ala Phe Pro Cys Gly Gly Gly Gly Lys Met Gly Glu Asn
            20                  25                  30

Ser Gly Ala Leu Ser Ala Gln Ala Ala Val Gly Pro Gly Gly Arg Ala
            35                  40                  45

Arg Pro Glu Val Arg Ser Met Val Asp Val Leu Ala Asp His Ala Gly
50                  55                  60

Glu Leu Val Pro Thr Asp Ser Pro Asn Phe Leu Cys Ser Val Leu Pro
65                  70                  75                  80

Ser His Trp Arg Cys Asn Lys Thr Leu Pro Val Ala Phe Lys Val Val
            85                  90                  95

Ala Leu Gly Asp Val Pro Asp Gly Thr Val Val Thr Val Met Ala Gly
            100                 105                 110

Asn Asp Glu Asn Tyr Ser Ala Glu Leu Arg Asn Ala Ser Ala Val Met
            115                 120                 125

Lys Asn Gln Val Ala Pro Phe Asn Asp Leu Arg Phe Val Gly Arg Ser
130                 135                 140

Gly Arg Gly Lys Ser Phe Thr Leu Thr Ile Thr Val Phe Thr Asn Pro
145                 150                 155                 160

Thr Gln Val Ala Thr Tyr His Arg Ala Ile Lys Val Thr Val Asp Gly
            165                 170                 175

Pro Arg Glu Pro Arg Arg His Arg Gln Lys Leu Glu Asp Gln Thr Lys
            180                 185                 190

Pro Phe Pro Asp Arg Phe Gly Asp Leu Glu Arg Leu Arg Met Arg Val
            195                 200                 205

Thr Pro Ser Thr Pro Ser Pro Arg Gly Ser Leu Ser Thr Thr Ser His
            210                 215                 220

Phe Ser Ser Gln Pro Gln Thr Pro Ile Gln Gly Thr Ser Glu Leu Asn
225                 230                 235                 240

Pro Phe Ser Asp Pro Arg Gln Phe Val Arg Ser Phe Ser Thr Leu Ser
            245                 250                 255

Thr Leu Leu Glu Ser Arg Phe Pro Asp Pro Arg Ile Tyr Tyr Thr Gly
            260                 265                 270
```

```
Ala Met Ser Ala Ala Phe Pro Tyr Ser Ala Thr Pro Ser Gly Thr Ser
        275                 280                 285

Ile Ser Ser Leu Ser Val Ala Gly Ile Ser Ala Thr Ser Arg Phe His
        290                 295                 300

His Thr Tyr Leu Pro Pro Tyr Pro Gly Ala Pro Gln Asn Gln Ser
305                 310                 315                 320

Gly Pro Phe Gln Ala Asn Pro Ser Pro Tyr His Leu Tyr Tyr Gly Thr
                325                 330                 335

Ser Ser Gly Ser Tyr Gln Phe Ser Met Val Ala Gly Ser Ser Ser Gly
            340                 345                 350

Gly Asp Arg Ser Pro Thr Arg Met Leu Ala Ser Cys Thr Ser Ser Ala
            355                 360                 365

Ala Ser Val Ala Ala Gly Asn Leu Met Asn Pro Ser Leu Gly Gly Gln
        370                 375                 380

Ser Asp Gly Val Glu Ala Asp Gly Ser His Ser Asn Ser Pro Thr Ala
385                 390                 395                 400

Leu Ser Thr Pro Gly Arg Met Asp Glu Ala Val Trp Arg Pro Tyr
                405                 410                 415

(2) INFORMATION FOR SEQ ID NO: 3:

(i) SEQUENCE CHARACTERISTICS:
        (A) LENGTH: 513 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 3:

Met Arg Ile Pro Val Asp Pro Ser Thr Ser Arg Arg Phe Ser Pro Pro
1               5                   10                  15

Ser Ser Ser Leu Gln Pro Gly Lys Met Ser Asp Val Ser Pro Val Val
            20                  25                  30

Ala Ala Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Glu Ala
    50                  55                  60

Ala Ala Ala Ala Ala Ala Ala Ala Ala Ala Ala Ala Ala Ala Ala Ala
65                  70                  75                  80

Ala Val Pro Arg Leu Arg Pro His Asp Asn Arg Thr Met Val Glu
            85                  90                  95

Ile Ile Ala Asp His Pro Ala Glu Leu Val Pro Thr Asp Ser Pro Asn
                100                 105                 110

Phe Leu Cys Ser Val Leu Pro Ser His Trp Arg Cys Asn Lys Thr Leu
            115                 120                 125

Pro Val Ala Phe Lys Val Val Ala Leu Gly Glu Val Pro Asp Gly Thr
        130                 135                 140

Val Val Thr Val Met Ala Gly Asn Asp Glu Asn Tyr Ser Ala Glu Leu
145                 150                 155                 160

Arg Asn Ala Ser Ala Val Met Lys Asn Gln Val Ala Arg Phe Asn Asp
                165                 170                 175

Leu Arg Phe Val Gly Arg Ser Gly Arg Gly Lys Ser Phe Thr Leu Thr
            180                 185                 190

Ile Thr Val Phe Thr Asn Pro Pro Gln Val Ala Thr Tyr His Arg Ala
```

-continued

```
            195                 200                 205
Ile Lys Val Thr Val Asp Gly Pro Arg Glu Pro Arg His Arg Gln
    210                 215                 220

Lys Leu Asp Asp Ser Lys Pro Ser Leu Phe Ser Asp Arg Leu Ser Asp
225                 230                 235                 240

Leu Gly Arg Ile Pro His Pro Ser Met Arg Val Gly Val Pro Pro Gln
                245                 250                 255

Asn Pro Arg Pro Ser Leu Asn Ser Ala Pro Ser Pro Phe Asn Pro Gln
                260                 265                 270

Gly Gln Ser Gln Ile Thr Asp Pro Gln Ala Gln Ser Ser Pro Pro
                275                 280                 285

Trp Ser Tyr Asp Gln Ser Tyr Pro Ser Tyr Leu Ser Gln Met Thr Ser
    290                 295                 300

Pro Ser Ile His Ser Thr Thr Pro Leu Ser Ser Thr Arg Gly Thr Gly
305                 310                 315                 320

Leu Pro Ala Ile Thr Asp Val Pro Arg Arg Ile Ser Asp Asp Asp Thr
                325                 330                 335

Ala Thr Ser Asp Phe Cys Leu Trp Pro Ser Ser Leu Ser Lys Lys Ser
                340                 345                 350

Gln Ala Gly Ala Ser Glu Leu Gly Pro Phe Ser Asp Pro Arg Gln Phe
                355                 360                 365

Pro Ser Ile Ser Ser Leu Thr Glu Ser Arg Phe Ser Asn Pro Arg Met
370                 375                 380

His Tyr Pro Ala Thr Phe Thr Tyr Thr Pro Pro Val Thr Ser Gly Met
385                 390                 395                 400

Ser Leu Gly Met Ser Ala Thr Thr His Tyr His Thr Tyr Leu Pro Pro
                405                 410                 415

Pro Tyr Pro Gly Ser Ser Gln Ser Gln Ser Gly Pro Phe Gln Thr Ser
                420                 425                 430

Ser Thr Pro Tyr Leu Tyr Tyr Gly Thr Ser Ser Ala Ser Tyr Gln Phe
                435                 440                 445

Pro Met Val Pro Gly Gly Asp Arg Ser Pro Ser Arg Met Val Pro Pro
                450                 455                 460

Cys Thr Thr Thr Ser Asn Gly Ser Thr Leu Leu Asn Pro Asn Leu Pro
465                 470                 475                 480

Asn Gln Asn Asp Gly Val Asp Ala Asp Gly Ser His Ser Ser Ser Pro
                485                 490                 495

Thr Val Leu Asn Ser Ser Gly Arg Met Asp Glu Ser Val Trp Arg Pro
                500                 505                 510

Tyr
```

(2) INFORMATION FOR SEQ ID NO: 4:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 4:

```
Gly Ala Phe Thr Tyr Ser Pro Thr Pro Val Thr Ser Gly Ile Gly Ile
1               5                   10                  15

Gly Met Ser Ala Met Gly Ser Ala Thr Arg Tyr His Thr Tyr Leu
```

(2) INFORMATION FOR SEQ ID NO: 5:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GATCATGGCT TACCCATACG ATGTTCCAGA TTACGCTGAA TTCT            44
```

(2) INFORMATION FOR SEQ ID NO: 6:

(i) SEQUENCE CHARACTERISTICS:
        (A) LENGTH: 1909 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 766..1515

(xi) SEQUENCE DESCRIPTION: SEQ ID NO: 6:

```
ATTGAGAGAA CAGAGAACAT GACAAGTACT TCTAGCTCAG CACTGCTCCA ACTACTGAAG     60

CTGATTTTCA AGGCTACTTA AAAAAATCTG CAGCGTACAT TAATGGATTT CTGTTGTGTT    120

TAAATTCTCC ACAGATTGTA TTGTAAATAT TTTATGAAGT AGAGCATATG TATATATTTA    180

TATATACGTG CACATACATT AGTAGCACTA CCTTTGGAAG TCTCAGCTCT TGCTTTTCGG    240

GACTGAAGCC AGTTTTGCAT GATAAAAGTG GCCTTGTTAC GGGAGATAAT TGTGTTCTGT    300

TGGGACTTTA GACAAAACTC ACCTGCAAAA AACTGACAGG CATTAACTGG AACTTCCAAA    360

TAATGTGTTT GCTGATCGTT TTACTCTTCG CATAAATATT TTAGGAAGTG TATGAGAATT    420

TTGCCTTCAG GAACTTTTCT AACAGCCAAA GACAGAACTT AACCTCTGCA AGCAAGATTC    480

GTGGAAGATA GTCTCCACTT TTTAATGCAC TAAGCAATCG GTTGCTAGGA GCCCATCCTG    540

GGTCAGAGGC CGATCCGCAG AACCAGAACG TTTTCCCCTC CTGGACTGTT AGTAACTTAG    600

TCTCCCTCCT CCCCTAACCA CCCCCGCCCC CCCCACCCC CCGCAGTAAT AAAGGCCCCT    660

GAACGTGTAT GTTGGTCTCC CGGGAGCTGC TTGCTGAAGA TCCGCGCCCC TGTCGCCGTC    720

TGGTAGGAGC TGTTTGCAGG GTCCTAACTC AATCGGCTTG TTGTG ATG CGT ATC        774
                                                  Met Arg Ile
                                                   1

CCC GTA GAT GCC AGC ACG AGC CGC CGC TTC ACG CCG CCT TCC ACC GCG      822
Pro Val Asp Ala Ser Thr Ser Arg Arg Phe Thr Pro Pro Ser Thr Ala
      5                  10                  15

CTG AGC CCA GGC AAG ATG AGC GAG GCG TTG CCG CTG GGC GCC CCG GAC      870
Leu Ser Pro Gly Lys Met Ser Glu Ala Leu Pro Leu Gly Ala Pro Asp
 20                  25                  30                  35

GCC GGC GCT GCC CTG GCC GGC AAG CTG AGG AGC GGC GAC CGC AGC ATG      918
Ala Gly Ala Ala Leu Ala Gly Lys Leu Arg Ser Gly Asp Arg Ser Met
                 40                  45                  50

GTG GAG GTG CTG GCC GAC CAC CCG GGC GAG CTG GTG CGC ACC GAC AGC      966
Val Glu Val Leu Ala Asp His Pro Gly Glu Leu Val Arg Thr Asp Ser
         55                  60                  65

CCC AAC TTC CTC TGC TCC GTG CTG CCT ACG CAC TGG CGC TGC AAC AAG     1014
```

```
Pro Asn Phe Leu Cys Ser Val Leu Pro Thr His Trp Arg Cys Asn Lys
         70                  75                  80

ACC CTG CCC ATC GCT TTC AAG GTG GTG GCC CTA GGG GAT GTT CCA GAT      1062
Thr Leu Pro Ile Ala Phe Lys Val Val Ala Leu Gly Asp Val Pro Asp
     85                  90                  95

GGC ACT CTG GTC ACT GTG ATG GCT GGC AAT GAT GAA AAC TAC TCG GCT      1110
Gly Thr Leu Val Thr Val Met Ala Gly Asn Asp Glu Asn Tyr Ser Ala
100             105                 110                 115

GAG CTG AGA AAT GCT ACC GCA GCC ATG AAG AAC CAG GTT GCA AGA TTT      1158
Glu Leu Arg Asn Ala Thr Ala Ala Met Lys Asn Gln Val Ala Arg Phe
             120                 125                 130

AAT GAC CTC AGG TTT GTC GGT CGA AGT GGA AGA GGG AAA AGC TTC ACT      1206
Asn Asp Leu Arg Phe Val Gly Arg Ser Gly Arg Gly Lys Ser Phe Thr
             135                 140                 145

CTG ACC ATC ACT GTC TTC ACA AAC CCA CCG CAA GTC GCC ACC TAC CAC      1254
Leu Thr Ile Thr Val Phe Thr Asn Pro Pro Gln Val Ala Thr Tyr His
             150                 155                 160

AGA GCC ATC AAA ATC ACA GTG GAT GGG CCC CGA GAA CCT CGA AGA CAT      1302
Arg Ala Ile Lys Ile Thr Val Asp Gly Pro Arg Glu Pro Arg Arg His
165                 170                 175

CGG CAG AAA CTA GAT GAT CAG ACC AAG CCC GGG AGC TTG TCC TTT TCC      1350
Arg Gln Lys Leu Asp Asp Gln Thr Lys Pro Gly Ser Leu Ser Phe Ser
180             185                 190                 195

GAG CGG CTC AGT GAA CTG GAG CAG CTG CGG CGC ACA GCC ATG AGG GTC      1398
Glu Arg Leu Ser Glu Leu Glu Gln Leu Arg Arg Thr Ala Met Arg Val
             200                 205                 210

AGC CCA CAC CAC CCA GCC CCC ACG CCC AAC CCT CGT GCC TCC CTG AAC      1446
Ser Pro His His Pro Ala Pro Thr Pro Asn Pro Arg Ala Ser Leu Asn
             215                 220                 225

CAC TCC ACT GCC TTT AAC CCT CAG CCT CAG AGT CAG ATG CAG GAG GAA      1494
His Ser Thr Ala Phe Asn Pro Gln Pro Gln Ser Gln Met Gln Glu Glu
             230                 235                 240

GAC ACA GCA CCC TGG AGA TGT TAAGGCAGAA GTCAGTTCTT CTGTCCATCC         1545
Asp Thr Ala Pro Trp Arg Cys
245                 250

CTCTCCCCAG CCAGGATAGA GCTATCTTTT CCATCTCATC CTCAGAAGAG ACTCAGAAGA    1605

AAGATGACAG CCCTCAGAAT GCACGTTATG AGGAAGGCAG AATGTGGGTC TGTAATTCCT    1665

CCGTGTCCCT TCTCCCCCTC TGCAAACCGT CGTAACAATA ATAGTTCCTA ACACATGGGA    1725

CAATTGTGAG GATTAAATGA GTTAGCCTGC AGAAATCACT TGATGCACAG CACATGGGAA    1785

GCATTGTGTG TATTTATTAA TCCTTCACAA AGTCTTTGAG ATATATTTTT ATCAAATATT    1845

TAGCATGGAT CCCGGTACAC TTTCAATACT TAATAAATGG TCAATGTTAT TCTTTTTCAC    1905

TATT                                                                  1909

(2) INFORMATION FOR SEQ ID NO: 7:

(i) SEQUENCE CHARACTERISTICS:
        (A) LENGTH: 43 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 7:

Pro Arg Met His Tyr Pro Gly Ala Phe Thr Tyr Ser Pro Thr Pro Val
1               5                   10                  15

Thr Ser Gly Ile Gly Ile Gly Met Ser Ala Met Gly Ser Ala Thr Arg
```

```
                    20                  25                  30
Tyr His Thr Tyr Leu Pro Pro Pro Tyr Pro Gly
            35                  40

(2) INFORMATION FOR SEQ ID NO: 8:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 8:

Pro Arg Met His Tyr Pro Gly Ala Phe Thr Tyr Ser Pro Pro Val Thr
 1               5                  10                  15

Ser Gly Ile Gly Ile Gly Met Ser Ala Met Ser Ser Ala Ser Arg Tyr
                20                  25                  30

His Thr Tyr Leu Pro Pro Pro Tyr Pro Gly
            35                  40

(2) INFORMATION FOR SEQ ID NO: 9:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 9:

Pro Arg Met His Tyr Pro Gly Ala Phe Thr Tyr Ser Pro Pro Val Thr
 1               5                  10                  15

Ser Gly Ile Gly Ile Gly Met Ser Ala Met Ser Ser Thr Ser Arg Tyr
                20                  25                  30

His Thr Tyr Leu Pro Pro Pro Tyr Pro Gly
            35                  40

(2) INFORMATION FOR SEQ ID NO: 10:

(i) SEQUENCE CHARACTERISTICS:
        (A) LENGTH: 43 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

Pro Arg Met His Tyr Pro Gly Ala Phe Thr Tyr Ser Pro Thr Pro Val
 1               5                  10                  15

Ser Ser Gly Ile Gly Ile Gly Met Ser Ala Met Ser Thr Ala Thr Arg
                20                  25                  30

Tyr His Thr Tyr Leu Pro Pro Pro Tyr Pro Gly
            35                  40

(2) INFORMATION FOR SEQ ID NO: 11:

(i) SEQUENCE CHARACTERISTICS:
        (A) LENGTH: 39 amino acids
```

(B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 11:

Pro Arg Met His Tyr Pro Ala Thr Phe Thr Tyr Thr Pro Pro Val Thr
1               5                  10                  15

Ser Gly Met Ser Leu Gly Met Ser Ala Thr Thr His Tyr His Thr Tyr
            20                  25                  30

Leu Pro Pro Pro Tyr Pro Gly
        35

(2) INFORMATION FOR SEQ ID NO: 12:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 12:

Pro Arg Met His Tyr Pro Ala Thr Phe Thr Tyr Thr Pro Pro Val Thr
1               5                  10                  15

Ser Gly Met Ser Leu Gly Met Ser Ala Thr Thr His Tyr His Thr Tyr
            20                  25                  30

Leu Pro Pro Pro Tyr Pro Gly
        35

(2) INFORMATION FOR SEQ ID NO: 13:

(i) SEQUENCE CHARACTERISTICS:
        (A) LENGTH: 49 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 13:

Pro Arg Ile Tyr Tyr Thr Gly Ala Met Ser Ala Ala Phe Pro Tyr Ser
1               5                  10                  15

Ala Thr Pro Ser Gly Thr Ser Ile Ser Ser Leu Ser Val Ala Gly Ile
            20                  25                  30

Ser Ala Thr Ser Arg Phe His His Thr Tyr Leu Pro Pro Tyr Pro
        35                  40                  45

Gly (2) INFORMATION FOR SEQ ID NO: 14:

(i) SEQUENCE CHARACTERISTICS:
        (A) LENGTH: 49 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 14:

-continued

```
Pro Arg Met His Tyr Pro Gly Ala Met Ser Ala Ala Phe Pro Tyr Ser
1               5                   10                  15

Ala Thr Pro Ser Gly Thr Ser Ile Ser Ser Leu Ser Val Ala Gly Met
            20                  25                  30

Pro Ala Thr Ser Arg Phe His His Thr Tyr Leu Pro Pro Pro Tyr Pro
            35                  40                  45

Gly
```

ISOLATED NUCLEAR MATRIX TARGETING PEPTIDE

CROSS-REFERENCE TO RELATED APPLICATIONS

This application claims the benefit of priority to U.S. Serial No. 60/050,104, filed on Jun. 20, 1997, the contents of which are incorporated herein by reference.

GOVERNMENT FUNDING

The United States government may have rights to this invention pursuant to NIH Grants AR42262 and CA64148.

BACKGROUND OF THE INVENTION

Regulation of gene expression is linked to the organization of nuclear structure. The functional complexity of nuclear organization is reflected by the multiplicity of specialized nuclear substructures or regions that contribute to DNA replication and/or gene expression. Specialized regions found in most cell types include the nucleolus, RNA polymerase 11 transcription and processing domains, coiled bodies, PML domains, and Barr bodies (41–49).

A principal component of nuclear architecture is the filamentous ribonucleoprotein network known as the nuclear matrix, a developmentally modulated structure as reflected by its protein composition that is specific to tissue type and differentiation stage (30,31). The nuclear matrix is involved in gene localization, and also in the concentration and subnuclear localization of a broad spectrum of transcription regulatory factors required for cell type and tissue-restricted gene expression (30-35). For example, several DNA binding proteins have been identified which localize to and interact with the nuclear matrix, including SATB-1 (50), ARBP (51,52), Lamin B (53,54), NMP-1 (55) and NMP-2 (21,35).

One class of transcription regulatory factors which are key transactivators of tissue-specific genes of the hematopoietic and bone lineages are the AML (acute myeloid leukemia) family of proteins. Members of the human AML, class of proteins include AML-1 (Meyers et al. (1993) *Mol. Cell. Biol.* 13:6336–6345), AML-2 (Levanon et al. (1994) *Genomics* 23:425–432) and AML-3 (Levanon et al. (1994), supra.). These proteins are closely related to the murine polyomavirus enhancer core-binding proteins PEBP2αA and PEBP2αB, formerly identified as the murine leukemia enhancer CBF (core-binding factor) proteins. In fact, AML-3 is identical to its murine homolog PEBP2αA.

AML proteins and their closely related family members share a homologous DNA binding domain located in the C-terminus, referred to as the rhd (runt homology domain) based on its previous documentation in the Drosophila runt gene (12-18). Structurally, the AML proteins are all highly homologous, with greater than 90% homology within the rhd domain and greater than 60% identity overall (Meyers et al. (1996) *Oncogene* 13:303–312).

Subsequent to the cloning of AML-1, a larger alternatively spliced form of AML-1, AML-1B, was identified (Meyers et al. (1995) *Mol Cell. Biol.* 15(4):1974–1982). AML-1B contains additional sequences at the N- and C-termini, including a potent transactivation domain within the C-terminus. AML-1 and AML-3 (PEBP2αA) both bind the consensus enhancer core motif 5'-TGYGGT (Y=C or T) and heterodimerize with the non-DNA binding partner CBF-β (1, 11–14).

One trait of particular interest among certain AML-1 proteins is their susceptibility to multiple chromosomal translocations in lymphoid and myeloid leukemias. The t(8; 21) translocation, which is present in 12–5% of acute myeloid leukemia cases (1–4), maintains the DNA binding domain of AML-1, but replaces the C-terminal domain with sequences from the MTG8 gene on chromosome 8. The rare t(3:2) translocation also removes sequences C-terminal to the AML-1 DNA binding domain (5-7). The t(12;21. translocation fuses the transcription factor TEL to the N-terminus of AML-1B (8-10). Thus, at least a subset of human leukemias is directly associated with, specific reorganization of the AML-1 coding) region.

An understanding of the normal molecular mechanisms that mediate the biological activities of AML-1 transcription factors, such as transcriptional activity and association with sub-nuclear compartments involved in transcription, would thus clearly benefit the art.

SUMMARY OF THE INVENTION

The present invention provides compositions and methods for sub-nuclear targeting of compounds to the nuclear matrix of a cell. In particular, the invention provides peptides, hereafter referred to as "nuclear matrix targeting peptides," capable of delivering a variety of compounds to the nuclear matrix of a cell upon linking the compounds to the nuclear matrix targeting peptides and introducing the resulting targeted compounds into a cell.

A nuclear matrix targeting peptide (NMTP) is defined functionally as having the ability to deliver a compound to the nuclear matrix of a cell when the compound is linked to the NMTP. Thus, an NMTP acts as a sub-nuclear trafficking signal, directing selected compounds to the nuclear matrix where the compounds can, for example, be expressed, detected, transferred onto other biomolecules or modulate transcription of genes.

In one embodiment of the invention, the NMTP is derived from a nuclear matrix-associated protein. The term "derived from" as used herein means comprising an amino acid sequence corresponding to at least a portion of the amino acid sequence of a nuclear matrix-associated protein, wherein the portion is essential for association of the protein with the nuclear matrix. The term "derived from" as used herein also means comprising an amino acid sequence which is sufficiently homologous to at least a portion of the amino acid sequence of a nuclear matrix-associated protein so that the NMTP has the ability to target an agent to the nuclear matrix when the agent is linked to the NMTP. The term "nuclear matrix-associated protein" as used herein refers to a protein which is naturally found in the nuclear matrix domain of a cell as reflected by the ability to detect and/or isolate the protein from cellular fractions containing the nuclear matrix.

Nuclear matrix-associated proteins from which an NMTP can be derived include but are not limited to transcription factors, kinases, nucleases, phosphatases, acetylases and ubiquitinases. In a preferred embodiment, the NMTP is derived from a transcription factor, such as a member of the acute myeloid leukemia (AML) family of proteins. Nuclear matrix-associated AML proteins include, for example, AML-1B (SEQ ID NO:1), AML-2 (SEQ ID NO:2), and AML-3 (SEQ ID NO:3). In one embodiment, an NMTP comprises a portion of the C-terminus of AML-1B, preferably bases 351–381 of the full-length AML-1B protein (SEQ ID NO:1). This 31) amino acid peptide has the amino acid sequence shown in SEQ ID NO:4. Thus, the invention provides in a particular embodiment an NMTP which comprises all or a portion of the amino acid sequence shown in SEQ ID NO: 4, or an amino acid sequence having sufficient homology to all or a portion of the amino acid sequence shown in SEQ ID NO: 4 such that the peptide does not lose the ability to target an agent linked to the peptide to the nuclear matrix of a cell.

In another aspect, the invention provides a molecular complex comprising a nuclear matrix targeting peptide (NMTP) linked to an agent so that, upon introduction of the molecular complex into a cell, the agent is delivered to the nuclear matrix. The agent can be selected from a variety of compounds which can function in the nuclear matrix including but not limited to transcription factors, kinases, nucleases, phosphatases, acetylases and ubiquitinases, nucleic acids, nucleic acid modifying compounds, radiolabeled compounds and fluorescent compounds. In one embodiment, the agent is a transcription factor which regulates transcription of a gene. The terms "regulate" and "modulate" as used herein encompass both upregulation (e.g., increasing gene transcription and generally expression too) and downregulation (i.e., decreasing or inhibiting gene transcription and generally expression too).

In yet another aspect, the invention provides an antibody or antibody fragment directed against (i.e., reactive with) an NMTP as defined herein. Such antibodies and antibody fragments are useful, for example, to assess sub-nuclear localization of an NMTP or a compound linked to an NMTP. The antibody can be a polyclonal, monoclonal or humanized antibody.

In still another aspect, the invention provides an expression vector comprising a nucleotide sequence encoding an NMTP and a nucleotide sequence encoding at least one other protein selected for targeting to the nuclear matrix, such as a transcription factor, kinase, nuclease, phosphatase, acetylase or ubiquitinase. The nucleotide sequence encoding the NMTP and the nucleotide sequence encoding the at least one other protein are transcriptionally linked (i.e., positioned within the vector so that they are transcribed together as a single mRNA, which in turn is expressed as a single protein). Once expressed, the NMTP within the single protein serves to direct the protein to the nuclear matrix.

In yet another embodiment, the invention provides a method of delivering a compound to the nuclear matrix of a cell by linking the agent to an NMTP to form a targeted molecular complex, and then introducing the complex into a cell. NMTP-mediated targeting of compounds which regulate gene transcription, in particular, to the nuclear matrix permits selective regulation of gene transcription. Accordingly, the invention further provides a method for regulating transcription in a cell comprising introducing into the cell a targeted molecular complex comprising a nuclear matrix targeting peptide linked to a factor which regulates transcription of a gene. This method alternatively, can include introducing into the cell an expression vector encoding the targeted molecular complex which is then expressed in the cell and delivered to the nuclear matrix.

BRIEF DESCRIPTION OF THE FIGURES

FIG. 3 shows the homologous regions from human AML-2 (SEQ ID NO: 13) and human AML-3 (SEQ ID NO: 11), mouse AML-1B (SEQ ID NO:8) and mouse AML-3 (SEQ ID NO: 12), rat AML-1B (SEQ ID NO:9), and chicken AML-1B (SEQ ID NO:10) and chicken AML-2 (SEQ ID NO:14). Three motifs (boxes A, B, and C) show conservation of amino acids with either aliphatic (closed circle), aromatic (open circle), aliphatic hydroxyl (triangle) or basic (plus sign) side chains. The brackets denote segments with a propensity to form turns or a preponderance of hydrophobic or hydrophobic residues, based on the Kyte-Doolittle hydropathy plot using GCG software. The boxes to the far left and far right indicate amino acid motifs that are highly similar among AML genes, but dispensable for NMTS function.

DETAILED DESCRIPTION

Figure 1A:
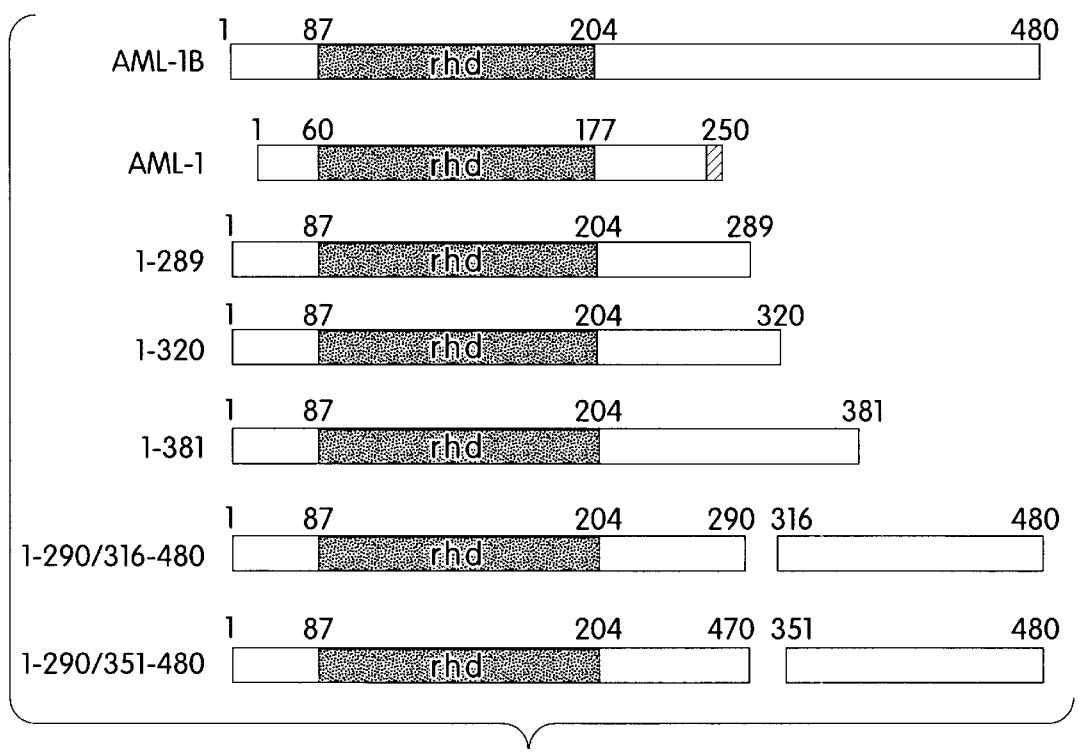
FIGS. 1A and 1B show schematic maps of various AML-1B deletion mutants used to delineate the transactivation domain in the C-terminus of the protein. The lightly shaded region labeled "rhd" represents the runt homology domain shared with AML-1. The dark shading shown in the AML-1 construct shown in Panel A designates amino acids unique to AML-1.

The nuclear matrix is involved in localization a broad spectrum of transcription regulatory factors and other proteins required for cell type and tissue-restricted gene expression (30-35). It has been discovered as part of the present invention that the specificity of these factors can be attributed to the presence of a nuclear matrix targeting sequence within the proteins. It has also been found that these nuclear matrix targeting sequences can operate independently, outside their natural sequence context, to deliver heterologous compounds to the nuclear matrix of a cell. Accordingly, the present invention provides a nuclear matrix targeting peptide (NMTP) derived from a protein which is naturally associated with the nuclear matrix wherein the NMTP is capable of delivering a heterologous compound to the nuclear matrix when the compound is linked to the NMTP.

As used herein, the term "linked" includes both covalent and non-covalent (e.g., electrostatic) linkages. Alternatively, the NMTP may be "linked" to a heterologous amino acid sequence by expressing the two sequences within a single protein (e.g., so that the NMTP and the heterologous sequence operate as two separate functional domains within a single protein). As used herein, the term "derived from" means comprising an amino acid sequence corresponding to at least a portion of the amino acid sequence of a nuclear matrix-associated protein, wherein the portion is essential for association of the protein with the nuclear matrix. The term "derived from" as used herein also means comprising an amino acid sequence which is sufficiently homologous to at least a portion of the amino acid sequence of a nuclear matrix-associated protein so that the NMTP has the ability to target an agent to the nuclear matrix when the agent is linked to the NMTP.

NMTPs derived from nuclear matrix-associated proteins can be isolated from native nuclear matrix-associated proteins by, for example, digestion (e.g., cleavage) of the native protein. Alternatively, they can be chemically synthesized using art recognized techniques. NMTPs can also be produced by recombinant expression of a nucleic acid encoding the NMTP in a host cell, followed by isolation of the NMTP from cell culture medium.

Nuclear matrix-associated proteins from which NMTPs can be derived include a variety of proteins which naturally occur in the nuclear matrix of cells. Such nuclear matrix-associated proteins include, for example, DNA binding proteins, transcription factors, kinases, nucleases, phosphatases, acetylases and ubiquitinases. Particular proteins which have been located in the nuclear matrix to date include SATB-1 (50), ARBP (51,52), Lamin B (53,54), NMP-1 (55), NMP-2 (21,35) and PML, bodies (48, 61–63).

To identify nuclear matrix-associated proteins (e.g., proteins which are naturally present in (e.g., localized within) or, alternatively, which have been targeted to the nuclear matrix e.g., via an NMTP, including those which interact with or are bound to the structural components of the nuclear matrix), a variety of art-recognized techniques and assays may be employed. Generally, cells extracts are fractionated to obtain nuclear matrix-containing fractions, followed by Western blot analysis, immunostaining or PAGE analysis of the nuclear matrix-containing fractions to identify proteins of interest. One method in particular which can be used to identify nuclear matrix-associated compounds is "the biochemical fractionation protocol" of Fey et al. (1984) *J. Cell Biol.* 98: 1973–1984. This method involves sequential detergent extractions of cells to obtain nuclear matrix/ intermediate filament preparations, followed by nuclease digestion and extraction with 0.25M ammonium sulfate. In one embodiment, sequential extractions are performed in CSK buffer containing e.g., 1.2 mMPMSF and 1% vanadyl ribonucleoside complex), nuclease digestion is performed using DNase, and extraction with 0.25M ammonium sulfate is performed using a high salt DB buffer containing 0.25M (NH)$_2$ SO$_4$ (see the Materials and Methods section of the Exemplification section and e.g., Example 1). Cellular fractions can then be screened for the presence of particular compounds by Western blot analysis or in situ immunostaining using antibodies directed against the nuclear matrix-associated compound, or analyzed on gels for the presence of previously unidentified compounds (e.g., proteins) which can then be isolated and further analyzed.

Another method which can be used to identify nuclear-matrix associated compounds is "the nuclear extraction protocol" or "salt-resistant nuclear retention assay" described in Meyers et al. (1995) *Mol. Cell. Biol.* 15:1974–1982. This method can be used to identify not only proteins present in the nuclear matrix of a cell preparation, but also proteins which are resistant to high salt extraction from the nuclear matrix, indicating stable anchoring or interaction with the nuclear matrix. As described in detail in the Examples below, "the nuclear extraction protocol" involves the preparation of in situ nuclear matrix samples by sequential incubation of cells in IsoHi buffer and high salt buffer. In one embodiment, the IsoHi buffer contains 10 mM Tris-Cl pH 8.4, 140 mM NaCl, 1.5 mM MgCl$_2$ 0.5% NP-40, and the high salt buffer contains 20 mM HEPES/pH 7.9, 1 M NaCl, 0.2 mM EDTA, 20% glycerol, 1.5 mM MgCl$_2$, 0.1 mM EGTA, 1.2 mM PMSF. This produces various cellular fractions, including cytoplasmic fractions, salt extractable nuclear fractions, and high salt-resistant nuclear "pellet" fractions. Compounds which are particularly stably associated with (e.g., anchored to) the nuclear matrix will be found in the high salt-resistant nuclear "pellet" fractions and can be identified using any known protein detection assay, such as Western blot analysis or immunostaining. Thus, the nuclear extraction method can be used to identify NMTPs which have the ability to deliver a heterologous compound to the nuclear matrix for stable association (e.g., anchoring) therewith.

In a particular embodiment of the invention, an NMTP is derived from a transcription factor which specifically associates with the nuclear matrix (e.g., is present in cellular fractions containing the nuclear matrix, but is substantially absent from cellular fractions not containing the nuclear matrix). Preferred transcription factors for deriving NMTPs include nuclear matrix-associated AML (acute myeloid leukemia) proteins. The term "AML protein" as used herein is includes not only human AML proteins, but also homologs of human AML proteins, such as the murine PEBP-2 family of proteins and homologous proteins from e.g., rat, chicken etc. Such homologs are known in the art and their identification has been described in numerous publications.

Particular AML proteins from which NMTPs can be derived include human AML-1B, AML-2, and AML-3 and homologs thereof. Full length cDNAs encoding human AML-1B (SEQ ID NO:1), AML-2 (SEQ ID NO:2), and AML-3 (SEQ ID NO:3) are publicly available from the American Type Culture Collection (ATCC). The full length nucleotide and amino acid sequences for AML-1 are also available from the Genbank database at accession number U19601, and are published in Meyers et al. (1995), supra. The full length amino acid sequences of human AML-2 (SEQ ID NO:2) and human AML-3 (SEQ ID NO:3) (which is identical to murine PEBP2α1) are published in Levanon et al. (1994) *Genomics* 23:425). The nucleotide and amino acid sequences for a variety of other AML homologs (e.g., mouse PEBP2 proteins) have also been published and/or are available from the Genbank database and/or the ATCC.

NMTPs can be identified and mapped within nuclear matrix-associated proteins, such as human AML proteins using e.g., deletion/function analysis. For example, a series of protein deletion mutants can be prepared either as mutant proteins or expressed from cDNAs encoding mutant proteins. These mutants can then be introduced or expressed within cells and tested for association with the nuclear matrix using protocols such as those previously described. Mutants which do not have the ability to associate with the nuclear matrix (e.g., which are not directed to the nuclear matrix) contain deletions which encompass an NMTS. The portion of the nuclear matrix-associated protein corresponding to these deletions can then be further mapped or can be tested for the ability to target a heterologous compound to the nuclear matrix when linked to the compound.

Figure 3:
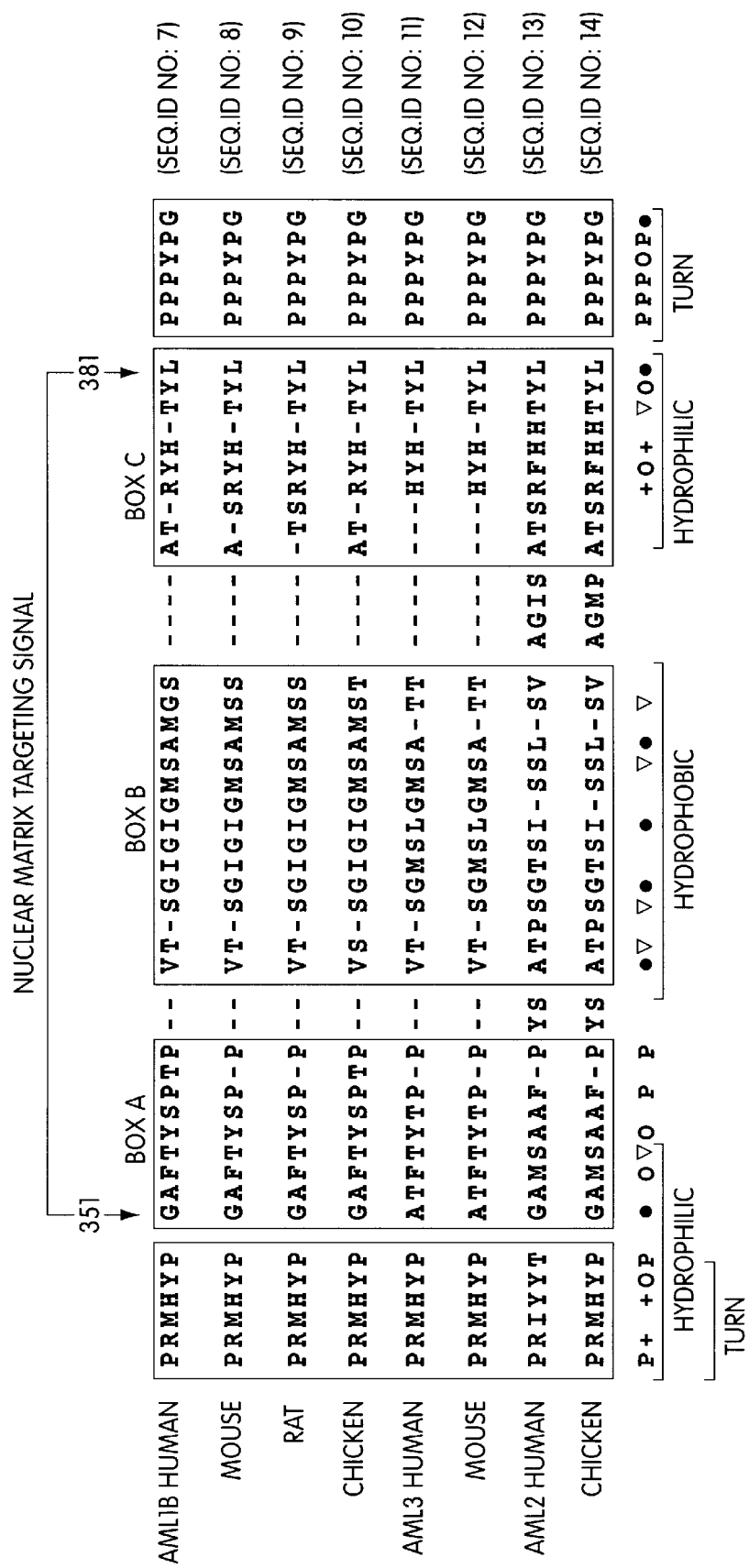
FIG. 3 shows a comparison of the amino acid sequence of the region in AML-1B containing the NMTS (SEQ ID NO: 7) with homologous regions in other members of the AML protein family, including human, mouse, rat and chicken AML proteins and homologs thereof. In particular.

In a particular embodiment, the invention provides an NMTP comprising amino acid bases 351–381 of the full-length AML-1B protein (SEQ ID NO:1), located within the C-terminus of the protein, as well as homologous, functional equivalents of this sequence as described below. This 31 amino acid peptide has the sequence: GAFTYSPTPVTSGIGIGMSAMGSATRYHTYL, (SEQ ID NO:4) and is shown in FIG. 3.

NMTPs of the present invention include not only peptides corresponding to a portion of a nuclear matrix-associated protein essential for nuclear matrix targeting of the protein, but also modified or homologous peptides which retain the ability to target heterologous compounds the nuclear matrix of a cell. Homology refers to sequence similarity between two NMTPs or between two nucleic acids encoding NMTPs. Homology can be determined by comparing a position in each sequence which may be aligned for purposes of comparison. When a position in the compared sequence is occupied by the same nucleotide base or amino acid, then the molecules are homologous at that position. A degree of homology between sequences is a function of the number of matching or homologous positions shared by the sequences.

One indication of a high degree of homology between nucleic acids and, thus, a high likelihood that the peptides encoded by the nucleic acids (e.g., NMTPs) have similar functions, is their ability to hybridize to one another under high or low stringency conditions. Appropriate stringency conditions which promote DNA hybridization, for example, 6.0×sodium chloride/sodium citrate (SSC) at about 45° C., followed by a wash of 2.0×SSC at 50° are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Accordingly, the invention provides in a particular embodiment an NMTP which comprises the amino acid sequence shown in SEQ ID NO: 4, or an amino acid sequence having sufficient homology to the amino acid sequence shown in SEQ ID NO: 4 such that the peptide does not lose the ability to target a heterologous agent linked to the peptide to the nuclear matrix of a cell. The invention also provides a nucleic acid encoding an NMTP comprising the amino acid sequence shown in SEQ ID NO: 4, or an amino acid sequence having sufficient homology to the amino acid sequence shown in SEQ ID NO: 4 such that the peptide does not lose the ability to target a heterologous agent linked to the peptide to the nuclear matrix of a cell.

An NMTP having the ability to target a linked compound to the nuclear matrix of a cell can be produced by modification of the amino acid sequence of the NMTP shown in SEQ ID NO: 4, such as a substitution, addition, or deletion of an amino acid residue which is not directly involved in the targeting function of the peptide. It is also possible to modify the structure of an NMTP for such purposes as increasing solubility or enhancing therapeutic efficacy or stability (e.g., shelf life ex vivo and resistance to proteolytic degradation in vivo). Such modified peptides are considered functional equivalents of NMTPs as defined herein. A modified NMTP can also be produced in which the amino acid sequence has been altered, such as by amino acid substitution, deletion, or addition, to modify immunogenicity and/or reduce allergenicity, or to which a component has been added for the same purpose.

In order to enhance stability and/or reactivity, an NMTP can be modified to incorporate one or more polymorphisms in the amino acid sequence of the peptide resulting from any natural allelic variation. Additionally, D-amino acids, non-natural amino acids, or non-amino acid analogs can be substituted or added to produce a modified NMTP within the scope of this invention. Furthermore, an NMTP can be modified using polyethylene glycol (PEG) according to the method of A. Sehon and co-workers (Wie et al., supra) to produce a protein conjugated with PEG. In addition, PEG can be added during chemical synthesis of the NMTP. Other modifications of NMTPs include reduction/alkylation (Tarr, *Methods of Protein Microcharacterization,* J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology,* W H Freeman, San Francisco, Calif. (1980), U.S. Pat. No. 4,939,239; or mild formalin treatment (Marsh, (197 1) *Int. Arch. of Allergy and Appl. Immunol.,* 41: 199–215).

To facilitate purification and potentially increase solubility of an NMTP, it is possible to add an amino acid fusion moiety to the peptide backbone. For example, hexa-histidine can be added to the protein for purification by immobilized metal ion affinity chromatography (Hochuli, E. et al., (1988) *Bio/Technology,* 6: 1321–1325). In addition, to facilitate isolation of NMTPs free of irrelevant sequences, specific endoprotease cleavage sites can be introduced between the sequences of the fusion moiety and the peptide.

Site-directed mutagenesis of a nucleic acid encoding an NMTP can be used to modify the structure of the peptide by methods known in the art. Such methods may, among others, include polymerase chain reaction (PCR) with oligonucleotide primers bearing one or more mutations (Ho et al., (1989) Gene, 77: 51–59) or total synthesis of mutated genes (Hostomsky, Z. et al., (1989) *Biochem. Biophys. Res. Comm,* 161: 1056–1063). To enhance recombinant protein expression, the aforementioned methods can be applied to change the codons present in the nucleotide sequences of the invention to those preferentially utilized by the host cell in which the recombinant protein is being expressed (Wada et al., supra).

In another aspect, the invention provides a molecular complex comprising an NMTP linked to an agent so that, upon introduction of the molecular complex into a cell, the agent is delivered to the nuclear matrix. The agent can be selected from a variety of compounds which function is a desired manner within the nuclear matrix including but not limited to transcription factors, kinases, nucleases, phosphatases, acetylases and ubiquitinases, nucleic acids, nucleic acid modifying compounds, radiolabeled compounds and fluorescent compounds. In one embodiment, the agent is a transcription factor which regulates transcription of a gene. The terms "regulate" and "modulate" encompass both upregulation (e.g., increasing gene transcription and generally expression too) and downregulation (i.e., decreasing or inhibiting gene transcription and generally expression too). For example, the transcription regulatory factor can be 1,25$(OH_2)D_3$ (Vitamin D), dexamethasone, or TGFβ which are capable of regulating transcription of genes involved in e.g., osteoblast proliferation and differentiation.

As previously defined herein, the term "linked" includes both covalent and non-covalent (e.g., electrostatic) linkages. Covalent linkages of NMTPs with heterologous compounds can be achieved using a number of known techniques depending on the nature of the heterologous compound (e.g., nucleic acid, protein, chemical compound etc.). For example, for protein-NMTP linkages, peptide bonds can be formed with e.g., water soluble carbodiimides as described e.g., by Jung, G. et al. (1981) *Biochem. Biophys. Res. Commun.* 101: 599–606. Alternatively, disulfide bonds or strong noncovalent linkages such as avidin-biotin coupling can be used. When linking compounds non-covalently to an NMTP, electrostatic interactions can be utilized. For example, the NMTP can be modified so as to have an overall positive charge (e.g., by reaction with cationic compounds such as polylysine). The cationic NMTP will then form a non-covalent complex with negatively charged compounds, such as DNA or RNA. Preferably, the heterologous compound is linked to the NMTP in a manner which does not abolish and, more preferably, does not reduce the activity of the heterologous compound.

Alternatively, an NMTP may be "linked" to a heterologous amino acid sequence by expression of the NMTP together with the heterologous sequence within a single protein. If the heterologous sequence has functional activity (e.g., transcriptional activity), then the single protein will have at least two separate functional domains. One domain, the NMTP domain, will direct the protein to the nuclear matrix. The other domain can function within this location to, e.g., modulate transcription of selected genes.

Expression vectors which encode functional NMTPs or hybrid proteins containing NMTPs "fused" (linked) to heterologous proteins can be constructed using art-recognized techniques. Generally, the nucleotide sequence encoding the NMTP and any other sequence to be targeted to the nuclear matrix is contained in an appropriate vector (e.g., an expression vector), such as a plasmid. For example, the NMTP must be operably linked to appropriate genetic regulatory elements which are functional in the cell to be transformed. Such regulatory sequences include, for example, promoter sequences which drive transcription of the gene. Suitable promoters include a broad variety of viral promoters, such as SV40 and CMV promoters. Regulatory sequences required for gene expression, processing and secretion are art-recognized and can be selected to direct expression of an NMTP in an appropriate cell. Accordingly, the term "regulatory sequence", as used herein, includes promoters, enhancers and other expression control elements. Such regulatory sequences are known and discussed in Goeddel, *Gene expression Technology: Methods in Enzymology.* p. 185, Academic Press, San Diego, Calif. (1990). In the case where the NMTP is to be expressed together with a heterolgous protein (e.g., as a single hybrid protein), the nucleotide sequences encoding these proteins must be transcriptionally linked so that they are transcribed together within a single mRNA and then expressed as a single protein.

In yet another aspect, the invention provides an antibody or antibody fragment directed against (i.e., reactive with) an NMTP as defined herein. Such antibodies and antibody fragments are useful, for example, to determine the sub-nuclear location of an NMTP or a compound linked to an NMTP. The term "antibody" as used herein encompasses all forms of antibodies known in the art, such as polyclonal, monoclonal, chimeric, recombinatorial, single chain and humanized antibodies, as well as fragments thereof (e.g., F(ab')$_2$ fragments) which specifically bind to an NMTP.

In one embodiment, the anti-NMTP antibody is a monoclonal antibody. Monoclonal antiobodies capable of recognizing NMTPs of the invention can be prepared using methods well known in the art. Such methods are described, for example, in detail in U.S. Pat. No. 4,942,131 and U.S. Pat. No. 5,583,053, the contents of which are incorporated by reference herein. The term "monoclonal antibody," as used herein, refers to a population of antibody molecules that contain only one species of an antigen binding site capable of immunoreacting with a particular epitope of an NMTP. A monoclonal antibody composition thus typically displays a single binding affinity for an NMTP.

Monoclonal antibodies useful in the methods of the invention are directed to an epitope of an NMTP, such that complex formed between the antibody and the NMTP (also referred to herein as ligation) can be recognized in detection assays such as ELISA, RIA etc. A monoclonal antibody to an epitope of an NMTP can be prepared by using a technique which provides for the production of antibody molecules by continuous cell lines in culture. These include but are not limited to the hybridoma technique originally described by Kohler and Milstein (1975, *Nature* 256:495–497), and the more recent human B cell hybridoma technique (Kozbor et al. (1983) *Immunol Today* 4:72), EBV-hybridoma technique (Cole et al. (1985), *Monoclonal Antibodies and Cancer Therapy,* Alan R. Liss, Inc., pp. 77–96), and trioma techniques. Other methods which can effectively yield monoclonal antibodies useful in the present invention include phage display techniques (Marks et al. (1992) *J Biol Chem* 16007–16010).

In one embodiment, the antibody preparation applied in the subject method is a monoclonal antibody produced by a hybridoma cell line. Hybridoma fusion techniques were first introduced by Kohler and Milstein (Kohler et al. *Nature* (1975) 256:495–97: Brown et al. (1981) *J. Immunol* 127:539–46;Brown et al. (1980) *J Biol Chem* 255:4980–83; Yeh et al. (1976) *PNAS* 76:2927–31; and Yeh et al. (1982) *Int. J. Cancer* 29:269–75). Thus, the monoclonal antibody compositions of the present invention can be produced by immunizing an animal with an NMTP. The immunization is typically accomplished by administering the NMTP to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the phosphoprotein immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a membrane-associated form of phosphoprotein. These screening methods are well known to those of skill in the art, e.g., ELISA and/or flow cytometry.

A suspension of antibody-producing cells is then removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. Rat, rabbit and frog somatic cells can also be used. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in *Monoclonal Hybridoma Antibodies: Techniques And Applications,* Hurell (ed.) pp. 51–52 (CRC Press 1982)). Hybridomas produced according to these methods can be propagated in vitro or in vivo (in ascites fluid) using techniques known in the art.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Such antibodies are the equivalents of the monoclonal and polyclonal antibodies described above, but may be less immunogenic when administered to humans, and therefore more likely to be tolerated by the patient.

Chimeric mouse-human monoclonal antibodies (i.e., chimeric antibodies) reactive with NMTPs of the invention can be produced by recombinant DNA techniques known in the art. For example, a gene encoding the constant region of a murine (or other species) anti-NMTP antibody molecule is substituted with a gene encoding a human constant region. (see Robinson et al., International Patent Publication PCT/US86/02269; Akira, et al., European Patent Application 184,187; Taniguchi, M., European Patent Application 171, 496; Morrison et al., European Patent Application 173,494; Neuberger et al., PCT Application WO 86/01533; Cabilly et al. U.S. Pat. No. 4,816,567; Cabilly et al., European Patent Application 125,023; Better et al. (1988 *Science* 240:1041–1043); Liu et al. (1987) PNAS 84:3439–3443; Liu et al. (1987) *J. Immunol.* 139:3521–3526; Sun et al. (1987) PNAS 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559).

A chimeric antibody can be further "humanized" by replacing portions of the variable region not involved in antigen binding with equivalent portions from human variable regions. General reviews of "humanized" chimeric antibodies are provided by Morrison, S. L. (1985) Science 229:1202–1207 and by Oi et al. (1986) *BioTechniques* 4:214. Those methods include isolating, manipulating, and expressing the nucleic acid sequences that encode all or part of an immunoglobulin variable region from at least one of a heavy or light chain. Sources of such nucleic acid are well known to those skilled in the art and, for example, may be obtained from an anti-NMTP antibody producing hybridoma. The cDNA encoding the chimeric antibody, or fragment thereof, can then be cloned into an appropriate expression vector. Suitable "humanized" antibodies can be alternatively produced by CDR or CEA substitution (see U.S. Pat. No. 5,225,539 to Winter; Jones et al. (1986) *Nature* 321:552–525; Verhoeyan et al. (1988) *Science* 239:1534; and Beidler et al. (1988) *J. Immunol.* 141:4053–4060).

Monoclonal antibodies or fragments thereof suitable for use in the present invention (i.e., which recognize and specifically bind to NMTPs) can also be produced by other methods well known to those skilled in the art of recombinant DNA technology. Such alternative methods include the "combinatorial antibody display" method which identifies and isolates antibodies and antibody fragments having a particular antigen specificity, and can be utilized to produce monoclonal anti-NMTP antibodies (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with an NMTP immunogen as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152–156). A similar strategy can also been used to amplify human heavy and light chain variable regions from human antibodies (Larrick et al. (1991) *Methods: Companion to Methods in Enzymology* 2:106–10).

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System,* catalog no. 27-9400-01; and the Stratagene SurfZAP™ phage display kit, catalog no. 240612), examples of methods and reagents particularly amenable for use in generating a variegated anti-NMTP antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 2:1373–1377; Hoogenboom et al. (1991) *Nuc Acid Res* 19:4133–4137; and Barbas et al. (1991) *PNAS* 88:7978–7982.

NMTPs of the present invention can be used to deliver a variety of therapeutic and diagnostic compounds to the nuclear matrix of a cell. For example, labeled NMTPs and antibodies reactive with NMTPs can be used to determine the locations of nuclear matrix associated proteins under normal and abnormal conditions, providing insight into the mechanisms behind particular disease phenotypes.

NMTPs can also be used to modify the nuclear architecture of a cell by delivering compounds to the nuclear matrix.

In particular embodiments, the NMTP can stably transfer a heterologous compound to the nuclear matrix so that the compound interacts with or binds (e.g., tightly) to the nuclear matrix filamentous structure, as judged for example, by resistance of the NMTP-linked compound to high salt extraction from nuclear matrix-containing cell fractions. Thus, NMTPs of the invention are capable of transferring compounds onto the nuclear matrix structure for association therewith. For example, transcription regulatory factors can be delivered to the nuclear matrix which upregulate or downregulate exression of particular genes. These transcription regulatory factors can include, for example, $1,25(OH_2)D_3$ (Vitamin D), dexamethasone, TGFβ which are capable of regulating transcription of osteoblast proliferation and differentiation. Other chemotherapeutics known in the art can similarly be targeted to the nuclear matrix using NMTPs. Thus, because NMTPs control the localization of proteins to the nuclear matrix, they can be used to modify the distribution of transcription factors within the nucleus of a cell.

In one embodiment, the NMTPs are used to target transcription factors to the nuclear matrix to modulate transcription. In this embodiment, a promoter recognition sequence (e.g., DNA binding domain) can be included along with the NMTP (i.e., in a single fusion protein or complex) to localize the transcription factor to foci within the nuclear matrix which support RNA transcription. Preferably these foci contain active RNA polymerases (e.g., RNA polymerase II) which are necessary, together with promoter recognition and binding, to activate transcription. For example, when targeting AML transcription factors to the nuclear matrix, the AML-1B runt homology DNA binding domain, or a functionally equivalent sequence having promoter recognition capabilities, can be included with the NMTS to co-localize the transcription factor within the nuclear matrix with RNA polymerase II, thereby enabling the transcription factor to modulate (i.e., activate) transcription.

NMTPs and NMTP related constructs of the present invention (e.g., molecular complexes containing NMTPs, or expression vectors encoding NMTPs) can be delivered to cells either in vivo or in vitro as a composition along with a pharmaceutically acceptable carrier or diluent. The term "pharmaceutically acceptable carrier or diluent" is intended to include any biologically compatible vehicle which does not reduce the activity of the kinase inhibitor and which is physiologically tolerable to the patient. Such agents include a variety of solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Administration of NMTPs and NMTP related constructs of the invention as described herein can be in any pharmacological form including a therapeutically active amount of an NMTP alone or in combination with another therapeutic molecule. Administration of a therapeutically active amount of the therapeutic compositions of the present invention is defined as an amount effective, at dosages and for periods of time necessary to achieve the desired result (e.g., targeting of a heterologous compound to the nuclear matrix in functional form). For example, a therapeutically active amount of an NMTP or NMTP related construct may vary according to factors such as the disease state, age, sex, and weight of the individual, and the ability of antibody to elicit a desired response in the individual. Dosage regimens may be adjusted to provide the optimum therapeutic response. For example, several divided doses may be administered daily or the dose may be proportionally reduced as indicated by the exigencies of the therapeutic situation.

The NMTP or NMTP related construct may be administered in a convenient manner such as by injection (subcutaneous, intravenous, intraarticular etc.), oral administration, inhalation, or transdermal application. Depending on the route of administration, the active compound may be coated in a material to protect the compound from the action of enzymes, acids and other natural conditions which may inactivate the compound. For example, NMTP or NMTP related construct may be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27). The kinase inhibitor may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the NMTP or NMTP related construct in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the particular individual to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The NMTP or NMTP related construct should be administered for a sufficient time period to achieve the desired therapeutic or diagnostic result in a patient (e.g., regulation of endogenous genes, targeting of exogenous genes). The concentration of active compound in the drug composition will depend on absorption, inactivation, and other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

The invention shall be further described in the following working examples:

EXAMPLES

Materials and Methods

Construction of AML-1B and HA-Epitope Tagged Expression Vectors. Expression vectors were based on pcDNA/ampI and contain the CMV promoter and segments of the human AML-1B cDNA. Most AML-1B deletion mutants were constructed by inserting a C-terminal PCR fragment into the Bam HI site at aa 289 (which reconstitutes aa 290). Stop codons were included in the 3' PCR primer and PCR fragments were sequenced to confirm error-free amplification. AML 1–289 and 1–320 were derived from pCMV5/AML-1B by cutting with BamHI or SalI, respectively, followed by Klenow fill-in and insertion of a DNA segment encoding stop codons. The HA-epitope tag (11 amino acids) is encoded by the HA-oligonucleotide: 5'GATCATGGCTTACCCATACGATGTTCCAGAT1'AC GCTGAATTCT3'(SEQ ID NO: 5) The HA-tag was fused, in frame, with amino acids 27–480 of AML-1B (CMV/HA/AML-1B construct). CMV/HA constructs expressing AML 27–290, AML 27–346 and AML 27–381 were generated by cutting CMV/HA/AML-1B at the 3' end with BglII and, respectively, BamHI, SphI and BspMI followed by self-ligation. CMV/HA/AMLΔ155–258 was prepared by internal deletion of an MseI restriction fragment. Additional CMV/HA-AML constructs were prepared by subcloning the XbaI fragments of pCMV5-AML (27–290/351–381), pCMV5-AML (27–290/387–480) or pCMV5-AML (27–290/432–480) into the XbaI site of the CMV/HA construct. Plasmids were prepared using the Qiagen plasmid purification kit.

Cell Culture and Transfections. Jurkat cells were cultured in RPMI supplemented with 10% FCS (Bio Whitaker). Cos-7 and C33A cells were cultured in Dulbecco's modified Eagles medium withi 10% FCS. Rat ostcosarcoma cells (ROS 17/2.8) were grown at 37° C. in F12 medium (GIBCO) supplemented with 2% FCS and 5% horse serum. DEAE-dextran mediated transfection was performed with 15–20 µg of plasmid DNA mixed with 1.5 ml F12 serum-free medium containing 0.2 mg/ml DEAE Dextran and 0.05 mg/ml Chloroquine. Aliquots of 0.5 ml of this mixture were added per dish of a 6-well plate, and incubated for 1.5–2.0 hours at 37° C. Cells were subject to a 15% glycerol shock for 2 minutes, washed with PBS, refed, and harvested at 36–40 hours following transfection.

Cellular Fractionation. Nuclear matrix fractions were prepared by sequential extraction using "the biochemical fractionation protocol" (36) with CSK buffer (100 mM NaCl, 300 mM sucrose, 10 mM PIPES/pH 6.8, 3 mM $MgCl_2$, 1 mM EGTA, 0.5% Triton X-100, 100 µg/ml DNase 1, 50 µg/ml RNase A, 1.2 mM PMSF) followed by 0.25 M ammonium sulfate extraction. Nuclear fractions were also prepared using a second method, the "nuclear extraction protocol," (14) (also referred to as the "salt-resistant nuclear retention assay") by sequential incubations in IsoHi buffer (10 mM Tris-Cl/pH8.4, 140 mM NaCl, 1.5 mM $MgCl_2$ 0.5% NP-40) and high salt buffer (20 mM HEPES/p[H7.9, 1 M NaCl, 0.2 mM EDTA, 20% glycerol, 1.5 mM $MgCl_2$, 0.1 mM EGTA. 1.2 mM PMSF). Western blot analysis was performed by electrophoresis in 10% or 12% SDS-PAGE gels. Proteins were transferred to a solid support, and detected with AML or HA antibodies (1:3000 dilution) using chemiluminescence (ECL, Amersham).

In Situ Nuclear Matrix Isolation and Indirect Immunofluorescence Analysis. In situ nuclear matrix samples were prepared by washing cells in PBS and extracting cells twice on coverslips in CSK buffer (containing 1.2 mMPMSF and 1% vanadyl ribonucleoside complex). DNase digestion was performed twice in DB buffer (as CSK buffer but containing 100 µg/ml DNase I and 50 mM NaCl) followed by extraction in DB buffer containing 0.25M $(NH)_2$ $SO_4$. The coverslips were fixed in 4% fomlaldellyde in PBS. Whole cell samples were fixed directly after the PBS wash, followed by permeabilization with 0.25% Triton X-100 in PBS. The primary antibody was incubated for 1–1.5 hours at 37° C. The primary antibodies were anti-HA (1:1500 dilution, 12CA5 mouse monoclonal, a gift from Dr. M. Czech), anti-NuMa (1:200 dilution rabbit polyclonal, a gift from, Matritech), anti-AML-1 (1:200 dilution, rabbit polyclonal against the N-terminal peptide of AML-1). The secondary antibody was incubated for 1 hour at 37° C. and was either a FITC-conjugated goat anti-rabbit antibody (1:400 Jackson Res. Lab.) or a Texas Red-conjugated donkey anti-mouse antibody (1:400 Jackson Res. Lab.). DNA content was evaluated by DAPI staining (5 µg/ml DAPI in PBS containing BSA and 0.05% Triton X-100). Cells were mounted in Vectashield H-1000.

Example 1

Association of AML-1B AML-2 and AML-3 With the Nuclear Matrix

To demonstrate that AML-1B associates with the nuclear matrix, subcellular partitioning of AML-1B in Jurkat T cells was investigated using two different extraction protocols. In the first protocol ("the biochemical fractionation protocol" of (36)), nuclear matrix/intermediate filament (NM) preparations were obtained from Jurkat cells by sequential detergent extractions followed by nuclease digestion and extraction with 0.25M ammonium sulfate. This yielded cytoplasmic (CSK and RSB), chromatin (Nuclease), and nuclear matrix (NM) fractions. Western blot analysis of the fractions showed clearly that most of AML-1B is associated with the nuclear matrix fraction which was also positive for the nuclear matrix specific marker lamin B. These results show that AML-1B co-fractionates with the nuclear matrix in Jurkat cells and, thus, are present in the nuclear matrix in cells of both bone and hematopoietic lineages.

The second protocol involved nuclear extraction of Jurkat cells using the method described in Meyers et al. (1995), supra. (referred to herein as "the nuclear matrix protocol"), resulting in cytoplasmic (C), salt extractable nuclear (N) and high salt-resistant nuclear "pellet" (P) fractions. Protein representing equal cell numbers was loaded in each lane. Western blot analysis was performed using an affinity purified rabbit polyclonal anti-peptide antibody directed against the 17 amino acids of the N-terminus of AML-1 . The results showed that AML-1B resisted extraction by high salt To visualize the cellular distribution of AML proteins, immunofluorescence analysis was performed on whole cell (WC) and in situ nuclear matrix (NM) preparations obtained from ROS 17/2.8 osteosarcoma cells. Antibody staining was performed using the anti-peptide antibody directed against the 17 amino acids of the N-terminus of AML-1. DNA content was assessed by DAPI staining. Bicochemical analysis had previously shown ROS 17/2.8 cells contained AML-related transcription factors in their nuclear matrix (21). The results showed that endogenous AML-related factors are retained throughout the nuclear matrix preparations from which all chromatin detectable by DAPI staining has been removed. This finding supports the specific association of AML-related factors with the nuclear matrix.

Subcellular partitioning of AML-2 and AML-3 was also analyzed. AML-1 (250 amino acids, SEQ ID NO:6) is a splice variant of AML-1B (480 amino acids, SEQ ID NO:1) that lacks the C-terminal extension which is conserved among AML-1B (SEQ ID NO:1), AML-2 (SEQ ID NO:2) and AML-3 (SEQ ID NO:3). In this study, AML-1, AML-1B, AML-2 and AML-3 cDNAs were expressed in Cos-7 cells transfected by the DEAE-dextran procedure (14). Subcellular fractions prepared by the method of Fey et al. (1984), supra. were subjected to Western blot analysis with AML-specific antibodies. The results showed that AML-1B, AML-2 and AML-3 remain in the high salt resistant fraction (P), while AML-1 is extracted into both cytoplasmic (C) and nuclear (N) fractions and is absent from the salt resistant fraction (P). This demonstrates that molecular differences between AML-1 and AML-1B result in specific differences in their partitioning between subnuclear fractions. The observation that AML-1B, AML-2 and AML-3 all localize to the nuclear matrix-containing fraction suggests that association with the nuclear matrix is a property shared among these three AML family members.

Example 2
Nuclear Matrix Targeting of AML-1B is Independent of DNA Binding and CBF-β Interaction To determine whether nuclear matrix specificity (as measured by salt-resistant nuclear retention) of AML-1B is linked to its DNA binding capacity and protein/protein interactions with the AML partner CBF-β, subnuclear partitioning of AML-1proteins containing single amino acid substitutions in the runt homology domain (rhd) (37) was analyzed. Mutations were made which (1) affect DNA binding but not CBF-p interaction (K144M), (2) eliminate both activities (L14SD, F146Y), and (3) do not affect wild type function (L14SF). Nuclear extraction analysis was performed for each mutant using "the nuclear extraction protocol" of Meyers et al. (1995), supra., resulting in cytoplasmic (C), salt extractable nuclear (N) and salt-resistant nuclear pellet" (P) fractions. The results showed that each of these mutant proteins remained in the salt-resistant insoluble nuclear fraction (P), indicating that neither DNA binding nor CBF-β interaction is required for association with the nuclear matrix.

Further evidence for the independence of nuclear matrix attachment and DNA binding in AML-1B was afforded by in situ immunofluorescence analysis of a deletion mutant of AML-1B that had been HA-tagged and expressed in ROS 17/2.8 cells. This mutant had an internal deletion of amino acids 155 to 258 of SEQ ID NO: 1 (AMLΔ155–258) that removes the entire distal portion of the rhd-domain encompassing the critical protein motifs involved in DNA binding (38) and also an auxiliary determinant for nuclear localization (39). Immunostaining was performed on both whole cell (WC) and nuclear matrix (NM) fractions using a NuMa antibody (aNuMa) and/or an HA antibody (aHA) to detect HA/AML. The results showed that the AMLΔ155–258 mutant protein did not bind DNA but nevertheless resisted extraction from the nuclear matrix. These results clearly demonstrate that DNA binding is not necessary for nuclear matrix association in AML-1.

Example 3
The C-Terminal Domain of AML-1B is Required for Targeting to the Nuclear Matrix As demonstrated in the studies described in Example 1, AML-1B is associated with the nuclear matrix, while AML-1 is not. One difference between the two proteins is the C-terminal extension of AML-1B that is absent in AML-1 (see FIG. 1A) which contains a strong transcriptional activation domain (15). The importance of this C-terminal domain in linking AML to the nuclear matrix was established by constructing a shortened version of AML-1B (AML-1–289) corresponding to amino acids 1–289 of SEQ ID NO: 1. This construct was truncated beyond amino acid 289 and resembles the AML-1 (33 kD) splice variant that also lacks these C-terminal amino acids. AML-1–289 also differed from AML-1 beyond amino acid 268 due to the presence in AML-1 of a unique C-terminal 9 amino acid segment encoded by an alternative exon (exon 7A) (19) (see FIG. 1A). To determine sub-cellular partitioning of these proteins, biochemical fractionation was performed using the "biochemical fractionation protocol" of Fey et al. (1984), supra. The results showed that AML-1B remains entirely in the nuclear matrix fraction while AML 1–289 is not bound to the matrix but elutes completely with the chromatin fraction.

In addition, in situ immunofluorescence analysis of whole cells and nuclear matrices was performed in transfected ROS 17/2.8 cells expressing HA-tagged AML proteins. Visualization of the in situ nuclear matrix was achieved by immunostaining with an antibody that detects the nuclear matrix protein NuMA. Both AML-1B and AML 1–289 proteins showed a similar broad distribution throughout the nucleus. However, both biochemical and in situ assays showed that AML 1–289 is not present in the nuclear matrix while AML-1B is matrix associated. These results demonstrate that the C-terminus of AML-1B (amino acids 290–480 of SEQ ID NO:1) contains a segment essential for association with the nuclear matrix, referred to herein as a nuclear matrix targeting signal (NMTS).

Example 4
Mapping the Nuclear Matrix Targeting Signal of AML-1B

To determine the specific domain in the C-terminal region of AML-1B required for binding to the nuclear matrix, a series of HA-tagged C-terminal deletion mutants, as well as mutants with deletions in internal domains of AML-1B, were constructed. Subcellular location of these AML-1B mutants was then determined by immunofluorescence labeling using anti-HA antibody (Meyers et al. (1995), supra.) on nuclear matrix preparations made from ROS 17/2.8 cells grown on cover slips, and by Western blot analysis of subcellular fractions (whole cell (WC) and in situ nuclear matrix preparations (NM)) using the procedure described in Example 3. The nuclear matrix protein NuMa was also localized as a control. Preparations were visualized with a FITC-conjugated secondary antibody detecting NuMa (ΔNuMa) and a Texas Red-conjugated antibody detecting the HA epitope (ΔHA). DNA was visualized by DAPI staining (DAPI). Regions of co-localization were detected by yellow appearance.

As shown by immunofluorescence analysis, AML 1–381 and AML 1–290/351–381, but not AML 1–346 and AML 1–290/439–480, associated with the nuclear matrix of ROS 17/2.8 cells. High resolution, computer enhanced images revealed that the staining, patterns for NuMa and AML-1B were dispersed and punctuated but non-overlapping. Constructs lacking the NMTS (AML1–346 and AML1–290/432–480) localized in the nucleus but were not retained in the nuclear matrix.

These results demonstrate that the amino acids between residues 351–381 of AML-1B (SEQ ID NO:1) contain a unique nuclear matrix targeting signal (NMTS) which is necessary for directing the rhd-containing portion of AML-1B (amino acids 1–289 of SEQ ID NO:1) to the nuclear matrix. The 31 amino acid sequence of the NMTS domain is shown in SEQ ID NO:4 and is as follows:

GAFTYSPTPVTSGIGIGMSAMGSATRYHTYL

This amino acid sequence is devoid of negatively charged amino acids and does not contain lysines, which are generally found in nuclear localization signals (NLS) (see e.g., Radu et al. (1995) *PNAS* 92:1769–1773); Twenty of the thirty-one amino acids of this NMTS (SEQ ID NO:4) are G.A,Y,T, or S.

Example 5
Mapping the Transactivation Domain of AML-1B

Figure 1B:
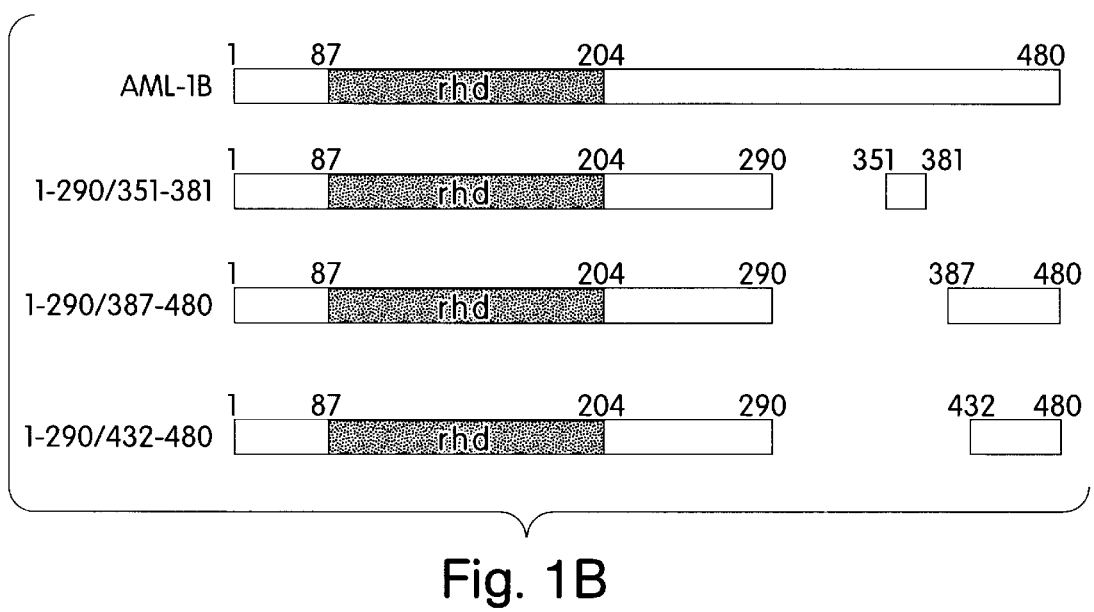

To map the specific domain in the C-terminal region of AML-1B (amino acids 290–480 of SEQ ID NO:1) containing the potent transactivation (TA) domain, transcription assays were performed using a series of C-terminal deletion mutants and also mutants with deletions in internal domains of AML-1B, as shown in FIGS. 1A and 1B. C33A cells were transfected by the calcium phosphate method (14) using 1 μg of TCRβ-CAT (25), pCMV5 or pCMV vectors expressing AML-1 or the AML-1B deletion mutants, and 5 μg of pRSV-LTR/SEAP expressing a secreted alkaline phosphatase gene (SEAP)(64). pBlueScript was added to bring each transfection to 25 μg of total DNA. Promoter activity was normalized for transfection efficiency using SEAP.

Figure 2A:
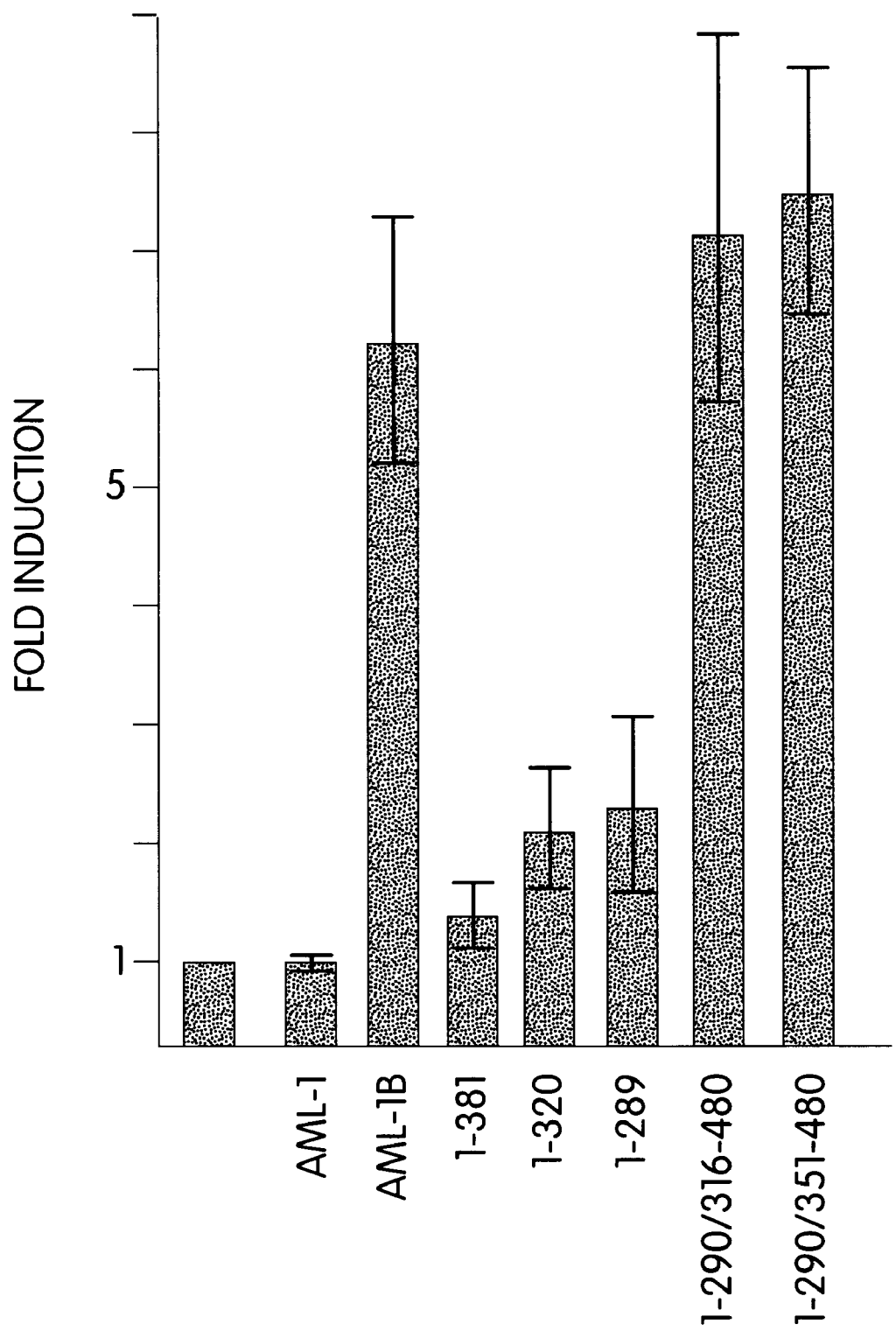
FIGS. 2A and 2B are bar graphs representing the level of transactivation induced by the various AML-1B deletion mutants shown in FIGS. 1A and 1B, respectively. Transactivation was assayed using the AML-1B responsive reporter gene construct TCRβ-CAT. The bar graph shows the fold induction of transcription with each AML protein as the average of three separate experiments (error bar=standard deviation).
Figure 2B:
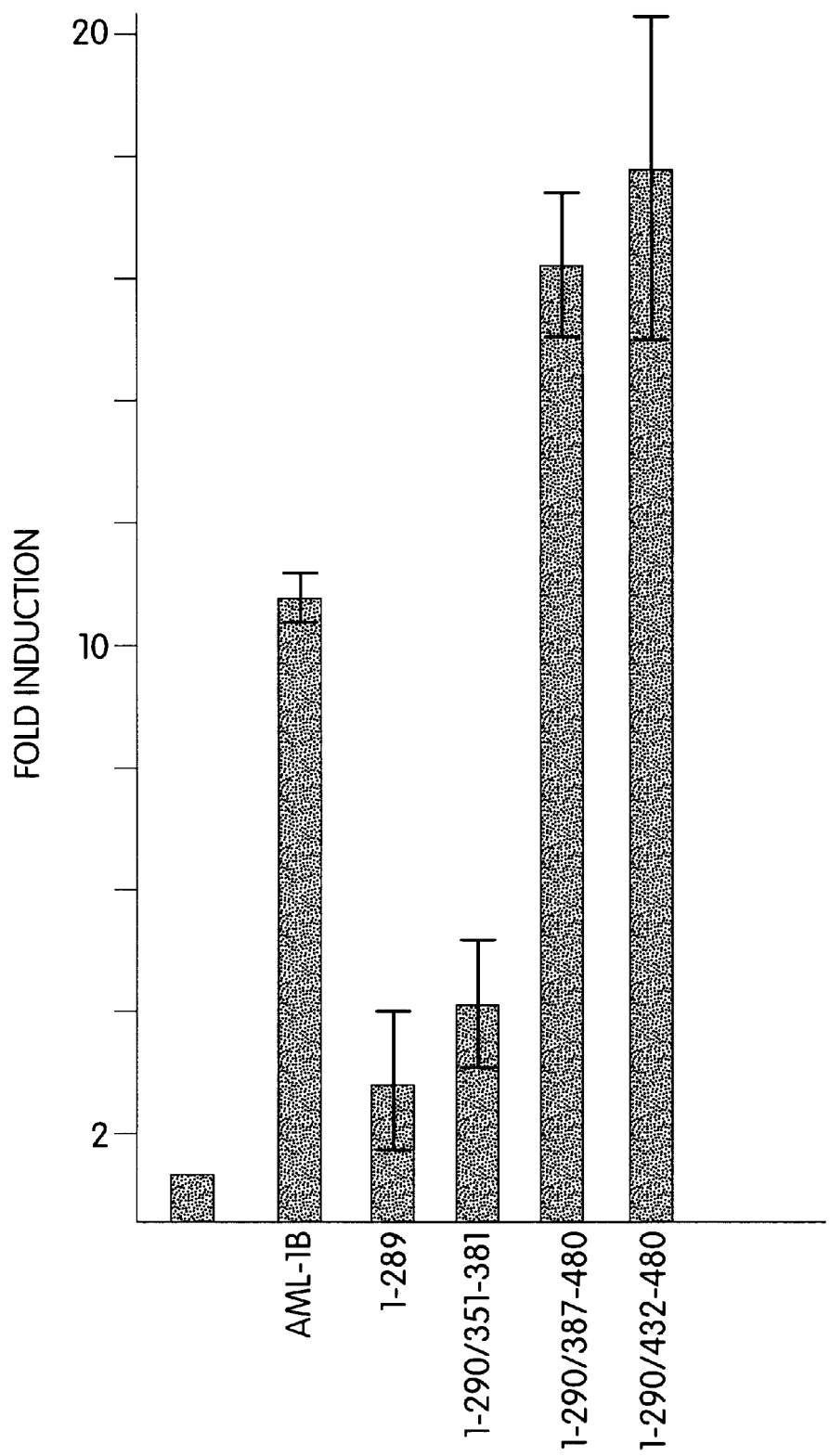

The results are shown in FIGS. 2A and 2B, demonstrating that absence of the C-terminal region (amino acids 290–480) in the AML1–289 protein (i.e., AML-1B with deletion of amino acids 1–289) correlates with dramatically reduced transactivation potential. Deletion of C-terminal residues 382–480 (AML1–381) abolishes transactivation. Internal deletions of either 291 to 315 (AML1–290/316–480) or 291 to 350 (AML 1–290/351–480) did not significantly reduce the transactivation potential of AML-1B (FIGS. 2A and 2B). It was also shown that AML 1–290/387–480 and AML 1–290/432–480 proteins were maximally active, whereas AML 1–290/351–381 was not (FIGS. 2A and 2B). These results clearly show that the main TA domain of AML-1B is found at the extreme C-terminus between amino acids 432–480 and is separable in vitro from the nuclear matrix targeting signal. However, both the TA domain (amino acids 432–480) and the NMTS (amino acids 351–381) are encoded by the same exon (exon 8 of the human AML-1 gene). Thus, although the TA and NMTS domains can be separated experimentally, the transactivation and nuclear matrix targeting functions are not dissociated in vivo.

Example 5
The NMTS is Sufficient to Target a Heterologous Nuclear Protein to the Nuclear Matrix To demonstrate nuclear-targeting ability (i.e., ability to direct and deliver a heterologous protein to the nuclear matrix (NM)) of the AML-1B NMTS delineated in Example 3, the NMTS was tested for its ability to target the GAL4 (1–147) protein to the nuclear matrix.

ROS 17/2.8 cells were transfected with expression vectors encoding GAL4(1–147) (protein alone) and GAL4(1–147) fused to the C-terminus of AML-1B (amino acids 171–480) (chimeric protein referred to as GAL4 (1–147)/AML 171–480). Cells were then extracted as previously described to obtain purified nuclear matrices, and the matrices were labeled for immunofluorescence with an antibody to GAL4. Fusion proteins were visualized using a GAL4 specific primary antibody and a FITC-conjugated secondary antibody. The results showed that the GAL4/AML-1B fusion protein bound to the nuclear matrix. In contrast, while the GAL4(1–147) protein is transported into the nucleus (40), it did not bind to the nuclear matrix. These results establish that the C-terminus of AML-1B represents an autonomous protein domain that confers association with the nuclear matrix.

To further test NMTS-mediated nuclear matrix targeting, gene segments encoding the NMTS (SEQ ID NO:4) corresponding to amino acids 351–381 of SEQ ID NO 1, or the TA domain corresponding to amino acids 432–480 of SEQ ID NO:1, were fused in frame with the N-terminal 147 residues of GAL4. The construct was then transfected into ROS 17/2.8 cells and analyzed for nuclear targeting in the same manner described for the GAL4 (1–147)/AML 171–480 construct. The results showed that the NMTS domain (GAL-4/AML 351–381 fusion protein), but not the T'A domain (GAL-4/AML 439–480 fusion protein), can direct association of the GAL4 protein with the nuclear matrix. This demonstrates that the NMTS of AML-1B (SEQ ID NO:4) is necessary and sufficient to target a heterologous protein to the nuclear matrix.

Example 6
Fusing the NMTS to the GAL4 DNA Binding Domain Transactivates a Genomically Integrated GAL4 Responsive Reporter Gene The following study was performed to demonstrate that the NMTS not only directs transcription factors to the nuclear matrix, but also functions as a transactivation domain when interacting with an appropriate promoter.

Transient Transfections

The AML-1B expression vector used to transfect cells was based on pcDNA/ampI and contained the cytomegalovirus (CMV) promoter and the human AML-1B cDNA linked to the hemagglutinin (HA)-tag fused in frame with aa 27 of AML-1B (CMV/HA/AML-1 construct). DEAE-dextran-mediated transfection was performed with 9 μg of plasmid DNA in 3 ml of F12 serum-free medium containing 0.2 mg/ml DEAE-dextran and 0.05 mg/ml chloroquine. Aliquots of 0.5 ml of this mixture were added to each well of a six-well plate and incubated for 1.5–2.0 hr at 37° C. SAOS cells were subject to a 15% glycerol shock for 2 min, washed with PBS, refed, and harvested at 24 hr following transfection. Identical results were obtained by transfection with lipofectantine using a protocol provided by GIBCO/BRL.

In Situ Nuclear Matrix Isolation and Indirect Immunofluorescence Analysis

In situ nuclear matrices were prepared as described (Fey et al. (1984) *J. Cell. Biology* 98:1973). Cells on coverslips were washed in PBS and extracted twice in CSK buffer (Fey et al. (1984) *J. Cell. Biology* 98:1973) for 15 minutes each. DNase digestion was performed twice in digestion buffer (CSK buffer with 50 mM NaCl) containing 100 μg/ml DNase I for 30 min, followed by extraction in digestion buffer containing 0.25 M $(NH_4)_2SO_4$ for 10 min. The coverslips were fixed in 4% formaldehyde in PBS. The primary antibody was incubated for 1–1.5 hr at 37° C. The primary antibodies were anti-HA (1:1,500 dilution, 12CA5 mouse mAb, a gift from M. Czech, University of Massachusetts Medical Center, Worcester, or a 1:1000 dilution of polyclonal anti-HA antibodies from Santa Cruz Biotechnology), anti-RNA polymerase $II_0$ (B3 mouse IgM mAb) that recognizes the hyperphosphorylated large subunit (250 kDa) of RNA polymerase II (Mortillaro et al. (1996) *PNAS* 93:8253–8257), anti-SC35 and anti-BrdUrd (Sigma). The secondary antibody was incubated for 1 hr at 37° C. and was either a fluorescein isothiocynate-conjugated goat anti-rabbit antibody (1:400, Jackson ImmunoResearch), a Texas red-conjugated donkey anti-mouse antibody (1:400, Jackson ImmunoResearch), or a rhodamine-conjugated goat anti-mouse IgM antibody. DNA content was evaluated by 4',6-diamidino-2-phenylindole staining (5 μg/ml 4',6-diamidino-2-phenylindole in PBS containing BSA and 0.05% Triton X-100). Cells were mounted in Vectashield H-1000. Microscopic images were obtained by using a CCD camera interfaced with a digital microscope system or a Bio-Rad MRC 1000 confocal microscope. Images were displayed by using the Adobe PHOTOSHOP program.

RNA Synthesis Inhibition and BrUTP Labeling

Cells were transfected as above for 21 hrs. Actinomycin D (5 μg/ml) or 5,6-dichlorobenzimidazole riboside (40 μg/ml) RNA synthesis inhibitors were added for 3 hr. The cells were harvested after 24 hr. BrUTP labeling was conducted on Triton X-100 permeabilized cells as described (27, 28).

Transactivation Assay

Transactivation assays were performed with HcLa GAL-5-Luc, a stable cell line carrying an integrated luciferase gene with five tandem GAL4 binding sites. This cell line was transfected with pCMV driven GAL4/AML-1B fusion proteins (250 ug pDNA per well) by using the polycation Superfect (Qiagen, Chatsworth, Calif.). Construct pCMV Sport β-galactosidase (GIBCO/BRL) was used as a control for transfection efficiency. Luciferase activity was used to calculate the average fold-induction relative to control (pCMV). Statistical comparisons were performed by using the unpaired Student's I test (STATVIEW II, MacIntosh).

Results

The NMTS of the AML Transcription Factor Acts as a Context-Dependent Activation Domain As demonstrated above in the previous Examples, the C-terminus of AML-1B contains a 31 amino acid NMTS (aa 351–381), as well as a transactivation domain (aa 432–480) that functions within the context of. e.g., the TCRβ promoter. In this Example, the C-terminal AML domain (aa 432–480) or the NMTS (aa 351–381) was tested for the ability to transactivate gene transcription when interacting with a heterologous promoter. Each of these two segments was fused separately to the GAL4 DNA binding domain (aa 1–147 of AML-1B). The results demonstrated that the fusion proteins expressed by these two constructs have very different activities when interacting with a promoter containing multiple GAL4 binding sites.

Figure 4:
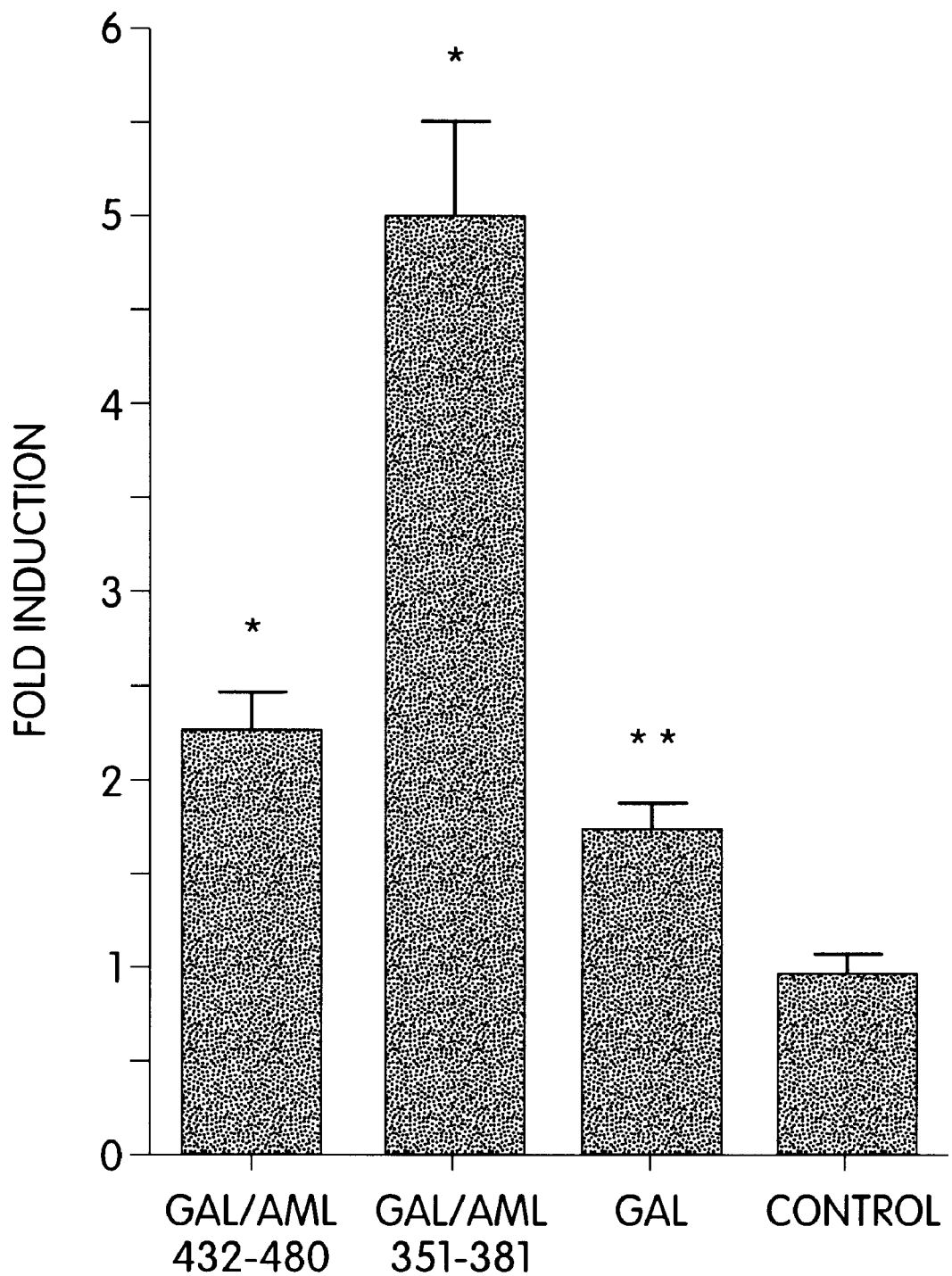
FIG. 4 is a bar graph showing the fold increase in expression of chromosomally integrated GAL reporter genes upon co-expression in cells of fusion proteins between the GAL4 DNA binding domain (aa 1-147;GAL) and C-terminal segments of AML-1B (GAL/AML 132-480 and GAL/AML 351-381 (NMTS)), relative to cells transfected with vector alone (control). Each bar represents data from 5 experiments (2-3 replicates). The asterisks indicate statistically significant differences relative to the control.

In particular, the transactivating activities of the two resulting GAL4/AML-1B fusion proteins were assayed by transfection and expression in a genetically modified HeLa cell line. This cell line contains a stably integrated reporter construct with five GAL4 responsive sites upstream of the TATA box that together drive the luciferase (LUC) gene. FIG. 4 shows the experimental results. Expression of the GAL4 (aa 1–147) protein alone results in, at most, a modest 1,5–2-fold increase over basal LUC activity (control). Fusing the C-terminal AML, (aa 432–480) segment to GAL4 has almost no effect on promoter activity. In contrast, the NMTS (aa 351–381) acts as a potent transactivation domain when assayed here with the GAL4 promoter (FIG. 4 shows that LUC activity is enhanced 5-fold relative to the control). This indicates that the NMTS is a context-dependent transactivation domain.

AML Regulatory Factors Associate with a Subset of RNA Polymerase II Domains on the Nuclear Matrix The finding that the NMTS (aa 351–381) domain affects both nuclear matrix targeting and transcriptional activation suggests that these two functions are causally related. One consequence of such a linkage would be the association of actively transcribing RNA polymerase II with AML-1B. To test this, double label immunofluorescence experiments were performed to ascertain the extent of colocalization of nuclear matrix-associated AML-1with the hyperphosphorylated form of RNA polymerase II (pol $II_0$). The results confirmed that RNA polymerase II domains associated with the nuclear matrix are transcriptionally active by immunofluorescence analysis of BrUTP-labeled RNA transcripts and RNA polymerase II in SAOS cells. The majority (>95%) of RNA polymerase II-containing foci were labeled with BrUTP. Therefore, the RNA polymerase 110 domains detected in SAOS cells with the B3 antibody used in this study represent sites of ongoing transcription.

In addition, human SAOS osteosarcoma cells were transfected with AML-1B tagged with the HA epitope, as described above. The cells were extracted to obtain the nuclear matrix, which was then labeled with antibodies to HA and to RNA polymerase $II_0$. The results showed that AML-1B and RNA polymerase $II_0$ molecules were bound to the nuclear matrix and distributed throughout the nuclear space. AML-1B was localized in a few prominent foci but most were more broadly distributed. RNA polymerase $II_0$ showed a similar but not identical distribution in large foci and in smaller domains throughout the nucleus. The number and size of RNA pol $II_0$ foci in SAOS cells showed cell-to-cell variation, possibly related to cell cycle stage and/or metabolic state. Strikingly, AML-1B and RNA polymerase $II_0$ colocalize at some of the most prominent foci in the nuclear matrix as well as at many of the smaller, more numerous sites. The colocalization of AML-1B and RNA polymerase $II_0$ suggests that nuclear matrix association of AML-1B is related to RNA polymerase II activity.

The foci labeled by fluorescent antibodies to AML-1B and polymerase $II_0$ were distinct from the RNA processing domains. Moreover, the results of the present study comparing the immunofluorescence pattern of AML-1B to that of SC-35 (a spliceosome assembly factor that is associated with domains enriched in splicing factor) showed that immunofluorescence signals for SC-35 and Ha/AML-1B antibodies do not overlap. Hence, AML-1B nuclear matrix domains clearly do not coincide with SC-35 domains.

Association of AML/CBFα to RNA Polymerase II Domains in the Nuclear Matrix Requires a Functional runt Homology DNA-Binding Domain In Example 5 above, it is shown that the NMTS in AML-1B is by itself sufficient to insure the association of the factor with the nuclear matrix. In the present Example, experiments were performed to determine whether auxiliary signals are required for colocalization of AML with transcriptionally active RNA polymerase $II_O$. In other words, the possibility was investigated that auxiliary signals are required along with the NMTS to target transcription factors to compartments within the nuclear matrix where transcription is active (i.e., containing transcriptionally active RNA polymerases). In particular, the role of the runt homology domain in establishing effective interactions of AML-1B with RNA polymerase $II_O$ at specific sites within the nucleus was assessed by analyzing the distribution of an AML-1B mutant (L148D). This mutant protein contains an amino acid substitution in the runt homology domain that abrogates recognition of gene-specific promoters. The results showed that there was no longer overlap with the RNA polymerase $II_O$ domains, indicating that a functional runt homology domain is essential for AML-1B to colocalize with RNA polymerase $II_O$. This result reinforces the proposal that promoter recognition plays an essential role in forming foci containing both AML-1B and active RNA polymerase II.

Conclusion

The results of the above-described studies indicate that the association of a transcription factor with the nuclear matrix is obligatory for its activity. In particular, these results show that the promoter-recognition function of the runt homology domain of AML-1B, and thus the consequential interactions with AML responsive genes, is essential for formation of transcriptionally active foci containing AML transcription factors and RNA polymerase II in the nuclear matrix.

Overall, these data provide evidence that targeting of AML/CBFα transcription factors to the nuclear matrix is important for their function in gene transcription. These data also demonstrate that, while the NMTS of AML transcription factors is sufficient alone for targeting to the nuclear matrix, additional promoter recognition sequences, such as the runt homology domain of AML-1B, are necessary along with the NMTS to target specific foci within the nuclear matrix which support RNA synthesis (i.e., containing transcriptionally active RNA polymerases).

Thus, the NMTS can be used, for example, to target associated (e.g., linked or fused) proteins to locations within the nuclear matrix containing genes which are poised but not fully competent to be transcribed. Alternatively, the NMTS can be used to target associated proteins to nuclear matrix domains which serve as inactive storage sites. Moreover, when linked to a promoter recognition sequence, the NMTS can also be used to target associated proteins (e.g., transcription factors) to sites which support transcription and to modulate (e.g., upregulate or downregulate) transcription at these sites.

Equivalents

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims. All references and patent documents referred to herein are hereby incorporated by reference in their entirety.

References

1. Miyoshi, H., Shimizu, K., Kozu, T., Maseki, N., Kaneko, Y. & Ohki, M. (1991) *Proc. Natl. Acad. Sci. USA* 88, 10431–10434.

2. Nisson, P. E., Watkins, P. C. & Sacchi, N. (1992) *Cancer Genet. Cylogenet.* 63, 81–88.

3. Erickson, P., Gao, J., Chang, K. S., Look, T., Whisenant, E., Raimondi, S., Lasher, R., Trujillo, J., Rowley, J. & Drabkin, H. (1992) *Blood* 80, 1825–1831.

4. Downing, J. R., Head, D. R., Curcio-Brint, A. M., Hulshof, M. G., Motroni, T. A., Raimondi, S. C., Carroll, A. J., Drabkin, 1—1. A., Willman, C., Theil, K. S., Civin, C.1. & Erickson, P. (1993) Blood 81, 2860–2865.

5. Mitani, K., Ogawa, S., Tanaka, T., Miyoshi, Shi, H., Kurokawa. M., Mano, H., Yazaki, Y., Ohki, M. & Hirai, H. (1994) EMBOJ. 13, 504–510.

6. Rubin, C. M., Larson, R. A., Anastasi, J., Winter, J. N., Thangavelu, M., Vardiman, J. W., Rowley, J. D. & LeBeau. M. M. (1990) Blood 76, 2594–2598.

7. Nucifora, G., Birn, D. J., Espinosa, R. I., Erickson, P., LeBeau, M. M., Roulston, D., McKeithan, T. W. Drabkin, H. & Rowley, J. D. (1993) Blood 81, 2728–2734.

8. Romana, S. P., Mauchauffe, M., Le Coniat, M., Chumakov, I., Le Paslier, D., Berger, R.,& Bernard, O. A. (1995) Blood 85, 3662–3670.

9. Golub, T. R., Barker, G. F., Bohlander, S. K., Hiebert, S. W., Ward, D. C., Bray-Ward, P., Morgan, E., Raimondi, S. C., Rowley, J. D. & Gilliland, D. G. (1995) Proc. Natl. Acad.Sci. U.S.A. 92, 4917–4921.

10. Romana, S. P., Poirel, H., Leconiat, M., Flexor, M.-A., Mauchauffe, M., Jonveaux, P., Macintyre, E. A., Berger, R. & Bernard, O. A. (1995) Blood 86, 4263–4969.

11. Ogawa, E., Inuzuka, M., Marnyama, M., Satake, M., Naito-Fujimoto, M., Ito, Y. & Shigesada, K. (1993) *Virology* 194, 314–331.

12. Wang, S., Wang, Q., Crute,. B. E., Mlelnikova, I. N., Keller, S. R. & Speck, N. A. (1993) Mol. Cell. Biol. 13, 3324–3339.

13. Meyers, S., Downing. J. R. & Hiebert, S. W. (1993) *Mol. Cell. Biol.* 13, 6336–6345.

14. Meyers. S., Lenny, N. & Hiebert, S. W. (1995) Mo. Cell. Biol. 15, 1974–1982.

15.Bae, S. C., Yamaguchi-Iwai, Ogawa, E., Maruyama, M., Inuzuka, M., Kagoshima, H., Shigesada, K., Satake, M. & Ito, Y. (1993).

16. Ogawa, E., Maruyama, M., Kagoshima, H., Inuzuka, M., Lu, J., Satake, M., Shigesada, K.& Ito, Y. (1993) *Proc. Natl. Acad. Sci. USA* 90, 6859–6863.

17. Levanon, D., Negreanu, V., Bernstein, Y., Bar-Am, I., Avivi. L. & Groner, Y. (1994) *Genomics* 23, 425–432.

18. Meyers, S., Lenny, N., Sun, W. H. & Hiebert, S. W. (1996) *Oncogene* 13, 303–12.

19. Miyoshi, H., Ohira, M., Shimizu, K., Mitani, K., Hirai, H., Imai, T., Yokoyama, K., Soeda, E. & Ohki, M. (1995) *Nucl. Acicls Res.* 23, 2762–2769.

20. Satake, M., Nomura, S., Yamaguchi-Iwai, Y., Takahama, Y., Hashimoto, Y., Niki, M., Kitamura, Y. & Ito, Y. (1995) *Mol. Cell. Biol.* 15, 1669–1670.

21. Merriman H L, Van Wijnen A J, Hiebert S, Bidwell .J P, Fey E, Lian J, Stein J & Stein G S.(1995) Bicohemistry 34, 13125–13139.

22Banerjec, C., Hiebert, S. W., Stein, J. L., Lian, J. B. & Stein, G. S. (1996) Proc. Natl. Acad Sci. U.S.A. 93, 4968–4973.

23. Nuchprayoon, I., Meyers, S., Scott, L. M., Suzow, J., Hiebert, S. W. & Friedman, A. D. (1994) *Mol. Cell. Biol.* 14. 555S–5568.

24. Ho, I.-C., Yang, L.-H., Morle, G. & Leiden, J. M. (1989) *Proc. Natl. Acad. Sci. USA* 86, 6714–6718.

25. Gottschalk, L. R. & Leiden, J. M. (1990) *Mol. Cell. Biol.* 10, 5486–5495.

26. Hernandez-Munain, C. & Krangel, M. S. (1994) *Mol. Cell. Biol.* 14, 473–483.

27. Frank, R., Zhang, J., Uchida, H., Meyers, S., Hiebert, S. W. & Nimer, S. D. (1995) *Oncogene* 11, 2667–2674.

28. Takahashi, A., Satake, M., Yamaguchi-Iwai, Y., Bae, S. C., Lu, J., Maruyama, M., Zhang, .Y. W., Oka, H., Arai, N., Arai, K.-I. & Ito, Y. (1995) *Blood* 86, 607–616.

29. Nimer, S., Zhang, J., Avraham, H & Miyazaki, Y. (1996) *Blood* 88, 66–74.

30. Nickerson, J. A., Blencowe, B. J. & Penman, S. (1995) in *The architectural organization of nuclear metabolism*. eds. Berezney, R. & Jeon, K. W. 67–123. 162A.

31. Stein G S, Van Wijnen A J, Stein J L, Lian J B, Bidwell J P & Montecino M. (1994) *J. Cell. Biochem.* 55, 4–15.

32. Blencowe, B. J., Nickerson, J. A., Issner, R., Penman, S. & Sharp, P. A. (1994) *J. Cell Biol.* 127, 593–607.

33. Mancini, M. A., Shan, B., Nickerson, J. A., Penman, S. & Lee, W.-E. (1994) *Proc. Natl. Acad. Sci. USA* 91, 418–422.

34. Van Wijnen A J, Bidwell J P, Fey E G, Penman S, Lian J B, Stein J L & Stein G S. (1993) *Biochemistry*32, 8397–8402.

35. Bidwell J P, Van Wijnen A J, Fey E G, Dworetzky S, Penman S, Stein J L, Lian J B & Stein G S. (1993) *Proc. Natl. Acad. Sci. USA* 90. 3162–3166.

36. Fey, E. G., Wan, K. M. & Penman, S. (1984). *J. Cell Biol.* 98, 1973–1984.

37. Lenny, N., Meyers, S. & Hiebert, S. (1995) *Oncogene* 11, 1761–1769.

38. Kurokawa, M., Tanaka, T., Tanaka, K., Hirano, N., Ogawa. S., Mitani, K., Yazaki, Y. & Hirai, H. (1996) *J. Biol. Chem.* 271, 16870–16876.

39. Lu,.T., Marnyama, M., Satake, M, Bae, S. C., Ogawa, E., Kagoshima, H., Shigesada, K. & Ito, Y. (1995) *Mo. Cell. Biol.* 15, 1651–1661.

40. Silver, P. A., Keegan, L. P. & Ptashine, M. (1984) *Proc. Natl. Acad. Sci. USA* 81, 5951–5955.

41. Carter, K. C., Bowman, D., Carrington, W., Fogarty, K., McNeil, J. A., Fay, F. S. & Lawrence, J. B. (1993) *Science* 259, 1330–1335.

42. Xing, Y., Johnson, C. V., Dobner, P. R. & Lawrence, J. B. (1993) *Science* 259, 1326–1330.

43. Fakan, S. (1994) *Trends Cell. Biol.* 4, 86–90.

44. Scheer, U., Thiry, M. & Goessens, G. (1993) *Trends Cell Biol.* 3, 236–241.

45. Spector, D. L. (1993) *Ann. Rev. Cell Biol.* 9, 265–315.

46. Brown, C. J., Hendrich, B. D., Rupert, J. L., Lafreniere, R. G., Xing, Y., Lawrence, J. & Willard, H. F. (1992) Cell 71, 527–542.

47. Clemson, C. M., McNeil, J. A., Willard, H. F. & Lawrence, J. B. (1996) *J. Cell Biol.* 132, 259–275.

48. Dyck, J. A., Maul, G. G., Miller, W. H., Chen, J. D., Kakizuka, A. & Evans, R. M. (1994) *Cell* 76, 333–343.

49. Matera, A. G. & Ward, D. C. (1993) *J. Cell Biol.* 121, 715–727.

50. Dickinson, L. A., Joh, T., KoLwi, Y. & KoLwi-Shigematsu, T. (1992) *Cell* 70, 631–645.

51. Buhrmester, H., von Kries, J. P. & Stratling, W. H. (1995) *Biochemistry* 34,4108–4117.

52. von Kries, J. P., Buhrmester, H. & Stratling, W. H. (1991) *Cell* 64, 123–135.

53. Luderus, M. E. E., de Graaf, A., Mattia, E., den Blaauwen, J. L., Grande, M. A., de Jong, L. & van Driel, R. (1992) *Cell* 70, 949–959.

54. Luderus, M. E. E., den Blaauwen, J. L,., de Smit, O. J. B., Compton, D. A. & van Driel, R. (1994) *Mol. Cell. Biol.* 14, 6297–6305.

55. Guo, B., Odgren, P. R., van Wijinen, A. J., Last, T. J., Nickerson, J., Penman, S., Lian, J. B., Stein, J. L. & Stein, G. S. (1995) *Proc. Natl. Acad. Sci. USA* 92, 10526–10530.

56. Wotton, D, Ghysdael, J., Wang, S., Speck, N. A. & Owen, M. J. (1994) *Mol. Cell. Biol.* 14, 840–850.

57. Giese, K., Kingsley, C., Kirshner, J. R. & Grosschedl, R. (1995) *Genes Dev.* 9, 995–1008.

58. Zhang, D. E., Hetherington, C. J., Meyers, S., Rhoades, K. L., Larson, C. J., Chen, H. M., Hiebert, S. W. & Tenen, D. G. (1996) *Mol. Cell. Biol.* 16, 1231–1240.

59. Miyoshi, H., Kozu, T., Shimizu, K., Enomoto, K., Maseii, N., Kaneko, Y., Kamada, N. & Ohki, M. (1993) *EMBO J.* 12, 2715–2721.

60. Hiebert, S. W., Sun, W., Davis, J. N., Golub, T., Shurtleff, S., Buijs, A., Downing, J. R., Grosveld, G., Roussell, M. 17. Gilliland. D. G. Lenny, N. & Meyers. S. (1996) *Mol. Cell. Biol.* 16, 1349–1355.

61. Carvalho, T., Seeler, J.-S., Ohman, K., Jordan, P., Pettersson, U., Akusjarvi, G., Carmo-Fonseca, M. & Dejean, A.(1995) *J. Cell Biol.* 131, 45–56.

62. Stuurman, N., de Graaf, A., Floore, A., Josso, A., Humbel, B., de.long, L. &: van Driel, R. (1992) *J. Cell Sci.* 101, 773–784.

63. Weis, K., Rambaud, S., Lavau, C., Jansen J., Carvalho, T., Carmo-Fonseca, M., Lamond, A & Dejean, A. (1994) *Cell* 76, 345–356

64. Berger, J., Hauber, J., Hauber, R., Geiger, R. & Cullen, B. R. (1988) Gene 66, 1–10.

65. Zeng et al. (1998) *PNAS* 95:1585–1589.

---

What is claimed is:

1. An isolated nuclear matrix targeting peptide comprising the amino acid sequence shown in SEQ ID NO:4, said peptide being capable of associating with the nuclear matrix of a cell.

2. A molecular complex comprising the nuclear matrix targeting peptide of claim 1 linked to an agent so that, upon introduction of the molecular complex into a cell, the agent is delivered to the nuclear matrix.

3. The molecular complex of claim 2 wherein the agent is selected from the group consisting of transcription factors, kinases, nucleases, phosphatases, acetylases and ubiquitinases.

4. The molecular complex of claim 2 wherein the agent is a nucleic acid.

5. The molecular complex of claim 2 wherein the agent is selected from the group consisting of radiolabeled and fluorescent compounds.

* * * * *